(12) United States Patent
Miyama et al.

(10) Patent No.: US 9,288,330 B2
(45) Date of Patent: Mar. 15, 2016

(54) SERVER, CONFERENCE ROOM MANAGEMENT METHOD OF SERVER, AND NETWORK CONFERENCE SYSTEM

(75) Inventors: Seiji Miyama, Kanagawa (JP); Masato Kajimoto, Chiba (JP); Kenji Yamane, Kanagawa (JP); Koichiro Kishima, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 157 days.

(21) Appl. No.: 13/251,494

(22) Filed: Oct. 3, 2011

(65) Prior Publication Data

US 2012/0096091 A1    Apr. 19, 2012

(30) Foreign Application Priority Data

Oct. 13, 2010 (JP) ................................. 2010-230632

(51) Int. Cl.
G06F 15/16 (2006.01)
H04M 3/56 (2006.01)
G06F 19/00 (2011.01)

(52) U.S. Cl.
CPC ............. H04M 3/567 (2013.01); G06F 19/321 (2013.01); G06F 19/3425 (2013.01)

(58) Field of Classification Search
CPC .................................. H04M 3/567; H04N 7/15
USPC ........................................................ 709/205
See application file for complete search history.

(56) References Cited

U.S. PATENT DOCUMENTS

| | | | |
|---|---|---|---|
| 5,617,539 A * | 4/1997 | Ludwig et al. ................. | 709/205 |
| 5,764,278 A * | 6/1998 | Nagao ........................... | 348/14.1 |
| 6,850,266 B1 * | 2/2005 | Trinca ......................... | 348/14.09 |
| 6,980,676 B2 * | 12/2005 | Pineau .......................... | 382/128 |
| 7,334,050 B2 * | 2/2008 | Zondervan et al. ........... | 709/246 |
| 7,716,283 B2 * | 5/2010 | Thukral ........................ | 709/204 |
| 8,190,674 B2 * | 5/2012 | Narayanan et al. ............ | 709/203 |
| 8,289,366 B2 * | 10/2012 | Greenwood et al. ....... | 348/14.08 |
| 8,423,612 B2 * | 4/2013 | Chen et al. .................... | 709/204 |
| 2001/0019587 A1 | 9/2001 | Hashimoto et al. | |
| 2002/0169832 A1 | 11/2002 | Lee et al. | |
| 2004/0230651 A1 * | 11/2004 | Ivashin ......................... | 709/204 |
| 2005/0244082 A1 | 11/2005 | Yamatake | |
| 2007/0005695 A1 * | 1/2007 | Chen et al. .................... | 709/204 |
| 2007/0115347 A1 * | 5/2007 | Yim ............................. | 348/14.08 |

(Continued)

FOREIGN PATENT DOCUMENTS

JP    2008-090715 A    4/2008
JP    2009-012802 A    1/2009

OTHER PUBLICATIONS

Nakamura, et al. (Jul. 1998,). A conference user interface supporting different access rights to shared hypermedia. In Computer Human Interaction, 1998. Proceedings. 3rd Asia Pacific (pp. 38-43). IEEE.*

*Primary Examiner* — Kristie Shingles
*Assistant Examiner* — Timothy Sowa
(74) *Attorney, Agent, or Firm* — Hazuki International, LLC

(57) ABSTRACT

A server connected to a client terminal via a network, includes a conference room management unit that manages a conference room for holding a conference, and a medical image holding unit that holds the predetermined number of medical image data including medical image data linked to the conference, wherein the conference room management unit manages one state which is a conference live state and other states which are different from the one state as a conference room state.

18 Claims, 21 Drawing Sheets

(56) References Cited

U.S. PATENT DOCUMENTS

| | | |
|---|---|---|
| 2009/0103790 A1 | 4/2009 | Yamagishi et al. |
| 2009/0135743 A1* | 5/2009 | Kowalewski ................. 370/261 |
| 2011/0125847 A1* | 5/2011 | Cocheu et al. ................ 709/204 |
| 2011/0126127 A1* | 5/2011 | Mariotti et al. ............... 715/753 |
| 2011/0238755 A1* | 9/2011 | Khan et al. .................... 709/204 |
| 2012/0046972 A1* | 2/2012 | Tonti et al. ........................ 705/3 |
| 2012/0069131 A1* | 3/2012 | Abelow ..................... 348/14.01 |
| 2012/0274725 A1* | 11/2012 | Robertson ................. 348/14.01 |

\* cited by examiner

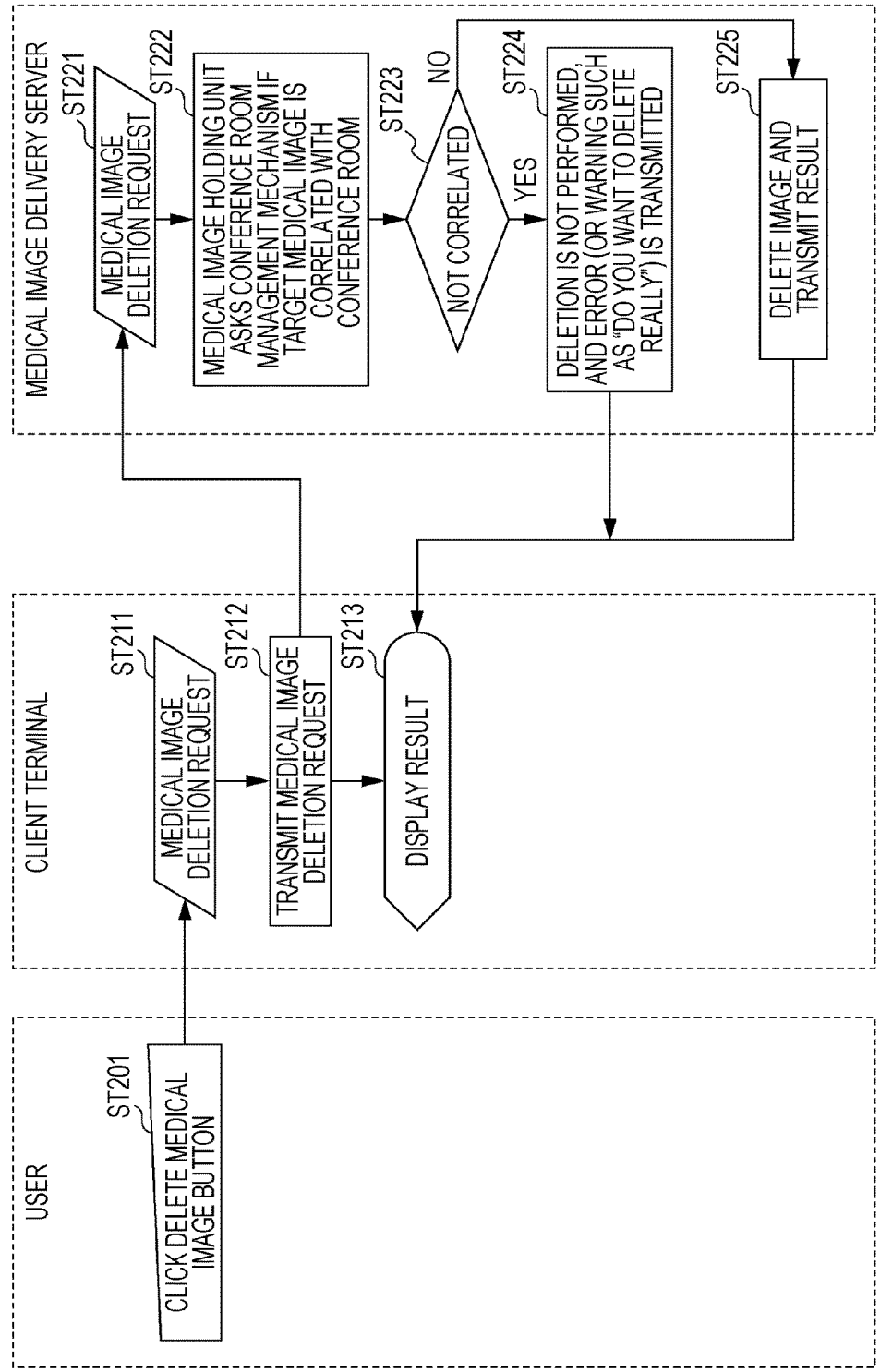

SERVER, CONFERENCE ROOM MANAGEMENT METHOD OF SERVER, AND NETWORK CONFERENCE SYSTEM

BACKGROUND

The present disclosure relates to a server, a conference room management method of the server, and a network conference system, and more particularly to a server and the like for holding a conference (case study session) using medical image data from a client terminal via a network.

In the related art, conferences (case conference) attended by a number of pathologists have been held on difficult cases. In the conferences in the related art, a number of pathologists commonly observe a pathology slide, which is physically managed, with a special optical microscope device.

In recent years, there has been proposed a system realizing a network conference by managing medical image data (DPI: Digital Pathology Imaging), which is digitalized by reading an image of the pathology slide with a scanner, on a server (refer to Japanese Unexamined Patent Application Publication No. 2009-12802). In this case, a client terminal side displays and observes a medical image by medical image data sent from a server on a viewer. The network conference system has advantages in that it is not necessary to physically manage pathology slides, the result of a case study is easily digitalized, remote pathologists can easily participate, and the like.

SUMMARY

In the network conference system which has been proposed in the related art, medical image data which is scheduled to be used in the conference may not be preannounced. For this reason, for example, a person who is scheduled to join the conference may not inspect and prepare for a medical image in advance. That is to say, in the network conference system which has been proposed in the related art, for example, a conference manager synchronously displays an open medical image on the respective client terminals during the conference.

In addition, in the network conference system which has been proposed in the related art, the conference may not be reviewed after the conference is closed. Therefore, for example, a person who did not join the conference may not confirm later what kind of screen operation was performed.

In addition, in the network conference system which has been proposed in the related art, comment information can be given to medical image data. However, in this system, there is no differentiation between comment information being given during the conference and that being given at a time other than the conference, and, for example, it is not possible to limit the inspectors depending on when the comment information is given.

It is desirable to realize a network conference system which is easily used according to a workflow of a doctor.

According to an embodiment of the present disclosure, there is provided a server connected to a client terminal via a network, including a conference room management unit that manages a conference room for holding a conference; and a medical image holding unit that holds the predetermined number of medical image data including medical image data linked to the conference, wherein the conference room management unit manages one state which is a conference live state and other states which are different from the one state as a conference room state.

In the embodiment, the conference room management unit manages a conference room for holding a conference. The medical image holding unit holds the predetermined number of medical image data including medical image data linked to the conference. The conference room management unit manages one state which is a conference live state and other states which are different from the one state as a conference room state. For example, the other states include a conference scheduled state positioned prior to the conference live state. In addition, for example, the other states include a conference stored state positioned after the conference live state.

As such, as a conference room state for holding a conference, there are one state which is a conference live state, and other states different from the one state. Therefore, it is possible to realize a network conference system which is easily used according to a workflow of a doctor.

For example, since there is the conference scheduled state as a conference room state, an advance notice of a conference can be given, and a person who is scheduled to join the conference can inspect a medical image in advance and prepare for the conference. In addition, since there is the conference stored state as a conference room state, it is possible to review the conference after the conference is closed.

The server may further include a comment information holding unit that holds comment information given to medical image data which is held in the medical image holding unit. The comment information holding unit may hold comment information given to the medical image data during the conference so as to be correlated with the conference, thereby differentiating the comment information from comment information given at other times. In this case, comment information given to medical image data can be held, and it is possible to easily differentiate whether or not the comment information is given during the conference.

The server may further include an image processing unit that performs a process for smoothly inspecting a medical image in the client terminal, for medical image data held in the medical image holding unit. For example, this process is compression of data. Through the data compression, the client terminals can smoothly inspect medical images because of the reduced communication amount during data transmission. In addition, for example, the process is encoding of data. Through the data encoding, the client terminals can smoothly inspect medical images because delay caused by encoding during data transmission can be removed.

Further, for example, the process is a change in data arrangement. In the data arrangement change, arrangement of medical image data is changed in terms of the storage order such as, for example, a "Hilbert order", and is held in an HDD (Hard Disk Drive) forming the medical image holding unit. Thereby, the client terminals can smoothly inspect medical images by reading the medical image data from the HDD at high speed.

Moreover, for example, the process is to copy or move medical image data to a storage medium which performs reading at high speed. For example, the medical image holding unit includes an SSD (Solid State Drive) in addition to the above-described HDD as a storage medium, and copies or moves the medical image data held in the HDD to the SSD. Thereby, for example, since the medical image holding unit reads accessed medical image data at high speed, the client terminals can smoothly inspect medical images.

In addition, for example, the image processing unit may preferentially perform the process for the medical image data which is scheduled to be used in the conference. Thereby, the client terminal can access the medical image data which is scheduled to be used in the conference and smoothly inspect medical images.

Further, the server may further include a medical image mark information holding unit that holds mark information which is selectively given to the predetermined number of the medical image data held in the medical image holding unit. In this case, the mark information given to medical image data can be held, and, for example, when a conference room is generated, it is possible to easily search for necessary medical image data by narrowing down image data using the mark information.

In addition, the server may further include a conference operation history data holding unit that holds operation history data during the conference. In this case, it is possible to reproduce a conference using the held conference operation history data after the conference is closed.

Further, the server may further include a time marker holding unit that holds time markers indicating remarkable points given to the conference on the time axis. For example, the time markers may be a first time marker given during the conference and/or a second time marker given during replay of the conference, and the time marker holding unit may hold the first and second time markers so as to be differentiated from each other. In this case, when a conference is replayed, it is possible to know the remarkable points of the conference on the time axis through the time markers.

The conference room management unit may have a function of resuming a closed conference by transitioning the conference room state. Thereby, it is possible to resume a conference which is stopped in the middle.

In this case, for example, the other states may include a conference scheduled state positioned prior to the conference live state and a conference stored state positioned posterior to the conference live state, and the conference room management unit may have a function of resuming a closed conference by transitioning the conference room state from the conference stored state to the conference scheduled state or to the conference live state.

In addition, the server may further include a conference operation history data holding unit that holds operation history data during the conference, and the conference operation history data holding unit may hold operation history data obtained by adding operation history data during a conference of the resumed conference to copy data of operation history data during a conference of the closed conference, as operation history data during a conference of the resumed conference.

In this case, operation history data during the conference of the closed conference remains in the conference operation history data holding unit, and thus only the closed conference may be replayed (reproduced) singly. In addition, operation history data during the conference of the resumed conference includes the operation history data of the closed conference, and thus continuous replay (reproduction) including the closed conference may be performed.

Further, the medical image holding unit may generate a confirmation message when medical image data instructed to be deleted is linked to the conference. For this reason, it is possible to prevent a case where a user deletes necessary medical image data by mistake.

According to another embodiment of the present disclosure, there is provided a server connected to a client terminal via a network, including a conference room management unit that manages a conference room for holding a conference; a medical image holding unit that holds the predetermined number of medical image data including medical image data linked to the conference; and a comment information holding unit that holds comment information given to medical image data which is held in the medical image holding unit, wherein the comment information holding unit holds comment information given to the medical image data during the conference so as to be correlated with the conference, thereby differentiating the comment information from comment information given at other times.

In the embodiment, the conference room management unit manages a conference room for holding a conference. The medical image holding unit holds the predetermined number of medical image data including medical image data linked to the conference. The comment information holding unit holds comment information given to medical image data which is held in the medical image holding unit. In this case, the comment information holding unit holds comment information given to the medical image data during the conference so as to be correlated with the conference, thereby differentiating the comment information from comment information given at other times.

As such, in the embodiment of the present disclosure, the comment information holding unit holds comment information given to medical image data, and if the comment information is given during a conference, the comment information is held so as to be correlated with the conference. Therefore, it is possible to easily differentiate whether or not comment information given to medical image data is added during a conference.

According to the embodiments of the present disclosure, as a state of a conference room for holding a conference, there are one state which is a conference live state, and other states different from the one state, and, therefore, it is possible to realize a network conference system which is easily used according to a workflow of a doctor. In addition, according to the embodiments of the present disclosure, if comment information given to medical image data is added during a conference, the comment information is held so as to be correlated with the conference, and thus it is possible to easily differentiate whether comment information given to medical image data is add during the conference or at other times.

BRIEF DESCRIPTION OF THE DRAWINGS

FIG. 3 is a diagram illustrating joining a conference room, leaving the conference room, or the like.

FIG. 21 is a flowchart illustrating an example of the process flow in a user, a client terminal, and a medical image delivery server when a medical image is deleted.

DETAILED DESCRIPTION OF EMBODIMENTS

Hereinafter, embodiments of the present disclosure will be described. The description will be made in the following order.
1. EMBODIMENTS
2. MODIFIED EXAMPLE

1. Embodiments

Configuration Example of Network Conference System

Figure 1:
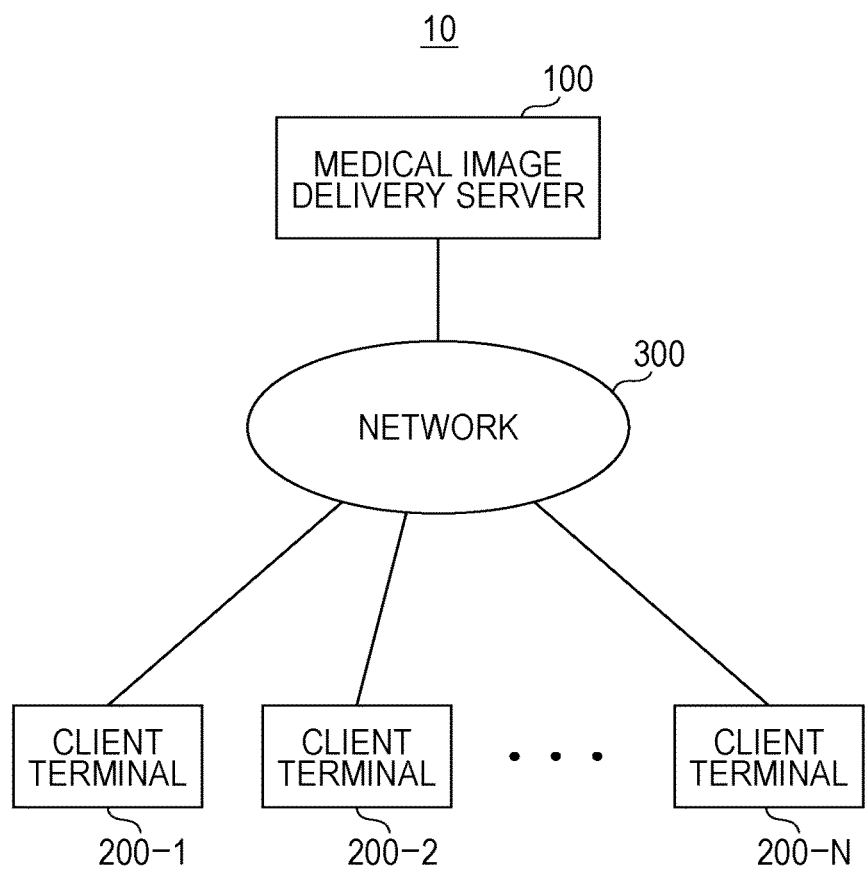
FIG. 1 is a block diagram illustrating a configuration example of a network conference system according to an embodiment of the present disclosure.

FIG. 1 shows a configuration example of the network conference system 10 according to an embodiment. The network conference system 10 includes a medical image delivery server 100, and the predetermined number of, here, N client terminals 200-1 to 200-N, connected to the server via a network 300.

Figure 2:
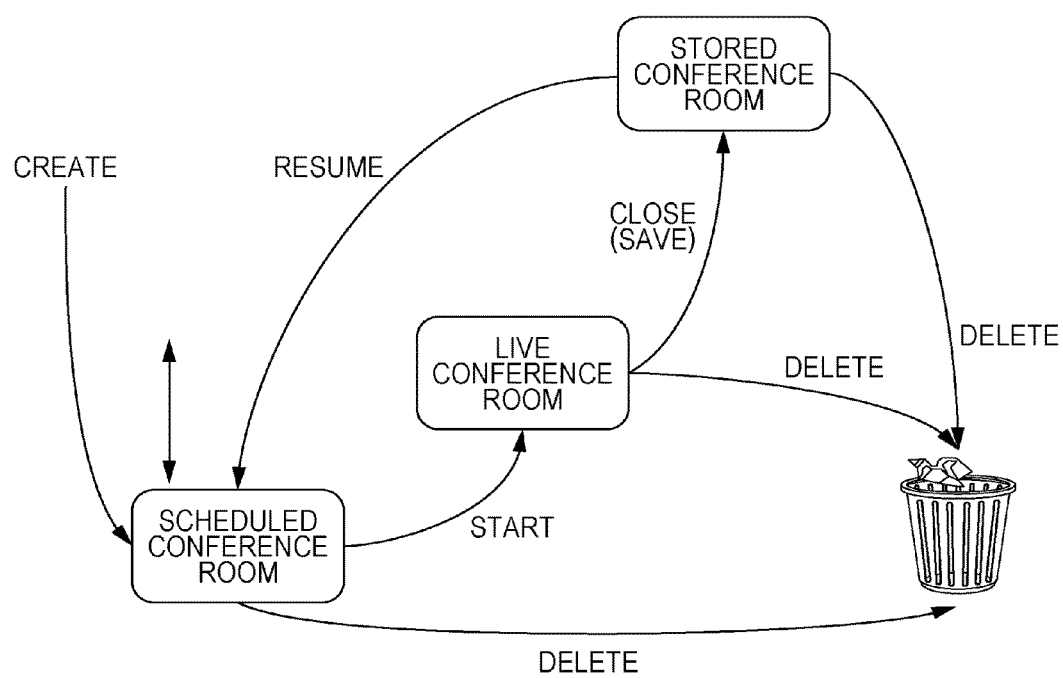
FIG. 2 is a state transition diagram illustrating a conference room having a conference scheduled state, a conference live state, and a conference stored state.

In the medical image delivery server 100, a conference room for holding a conference using medical image data is created in response to a creation operation. The conference room is correlated with medical image data used in a conference. The conference room transitions states as shown in FIG. 2. States of the conference room include a conference scheduled state, a conference live state, and a conference stored state. Here, the conference scheduled state indicates a state where a conference is scheduled to be held, and the conference live state indicates a state where the conference is being held. In addition, the conference stored state indicates a state where the conference is closed.

Figure 3:
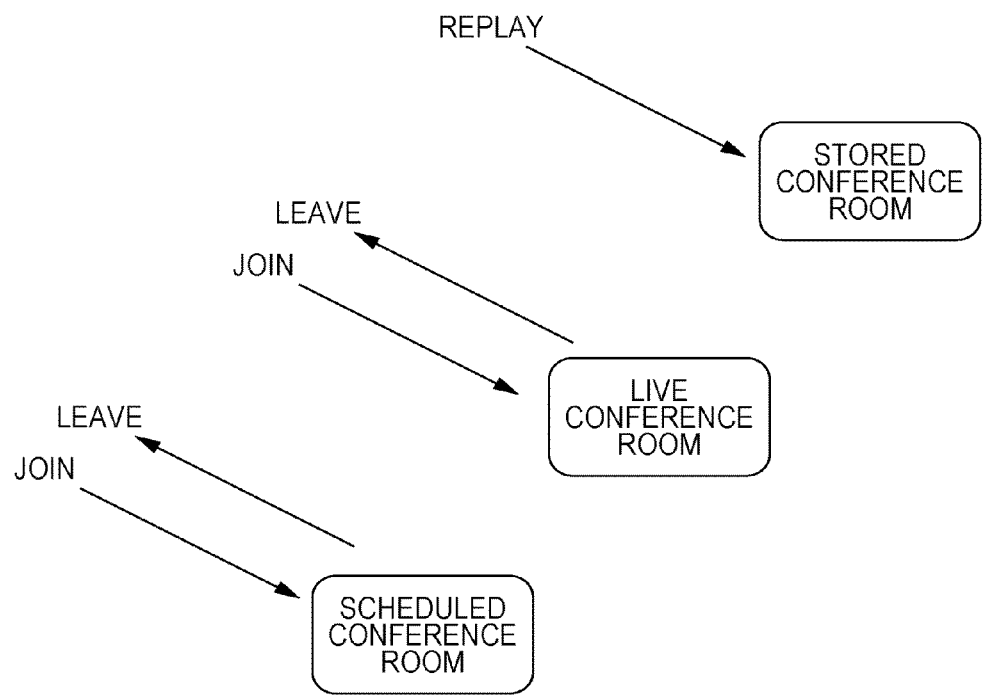

In a step where a conference room is created, the conference room is in a conference scheduled state. In this state, the client terminals 200-1 to 200-N can confirm the conference scheduled state. Users of the client terminals 200-1 to 200-N can join the conference room or leave the conference room in this state as shown in FIG. 3. In addition, in this state, a joining user can display and prepare for a medical image by medical image data correlated with the conference room on a viewer of a corresponding client terminal.

The conference room in the medical image delivery server 100 is transitioned from a conference scheduled state to a conference live state in response to a start operation as shown in FIG. 2, when the conference date comes. In this state, the client terminals of users joining the conference and the medical image delivery server 100 are connected to each other, and the conference is held.

When the conference is held, UI (User Interface) operations in the respective client terminals are synchronized with each other. That is to say, a screen operation or comment information is synchronized and thus the same display is performed in the respective client terminals. The users of the client terminals 200-1 to 200-N may join the conference or leave the conference in this state as shown in FIG. 3.

When the conference is closed, the conference room in the medical image delivery server 100 is transitioned from the conference live state to a conference stored state in response to a closing operation as shown in FIG. 2. In this state, the users of the client terminals 200-1 to 200-N may perform a replay operation and replay (reproduce) the closed conference room as shown in FIG. 3.

Further, in this state, in response to a resuming operation, the conference room is transitioned from the conference stored state to a conference scheduled state as shown in FIG. 2. Therefore, the closed conference can be resumed. In addition, in this case, the conference room may be transitioned to a conference live state instead of the conference scheduled state.

Further, the conference room created in the medical image delivery server 100 is deleted in response to a deletion operation as shown in FIG. 2. The deletion operation can be performed in any state of the conference scheduled state, the conference live state, and the conference stored state.

Figure 4:
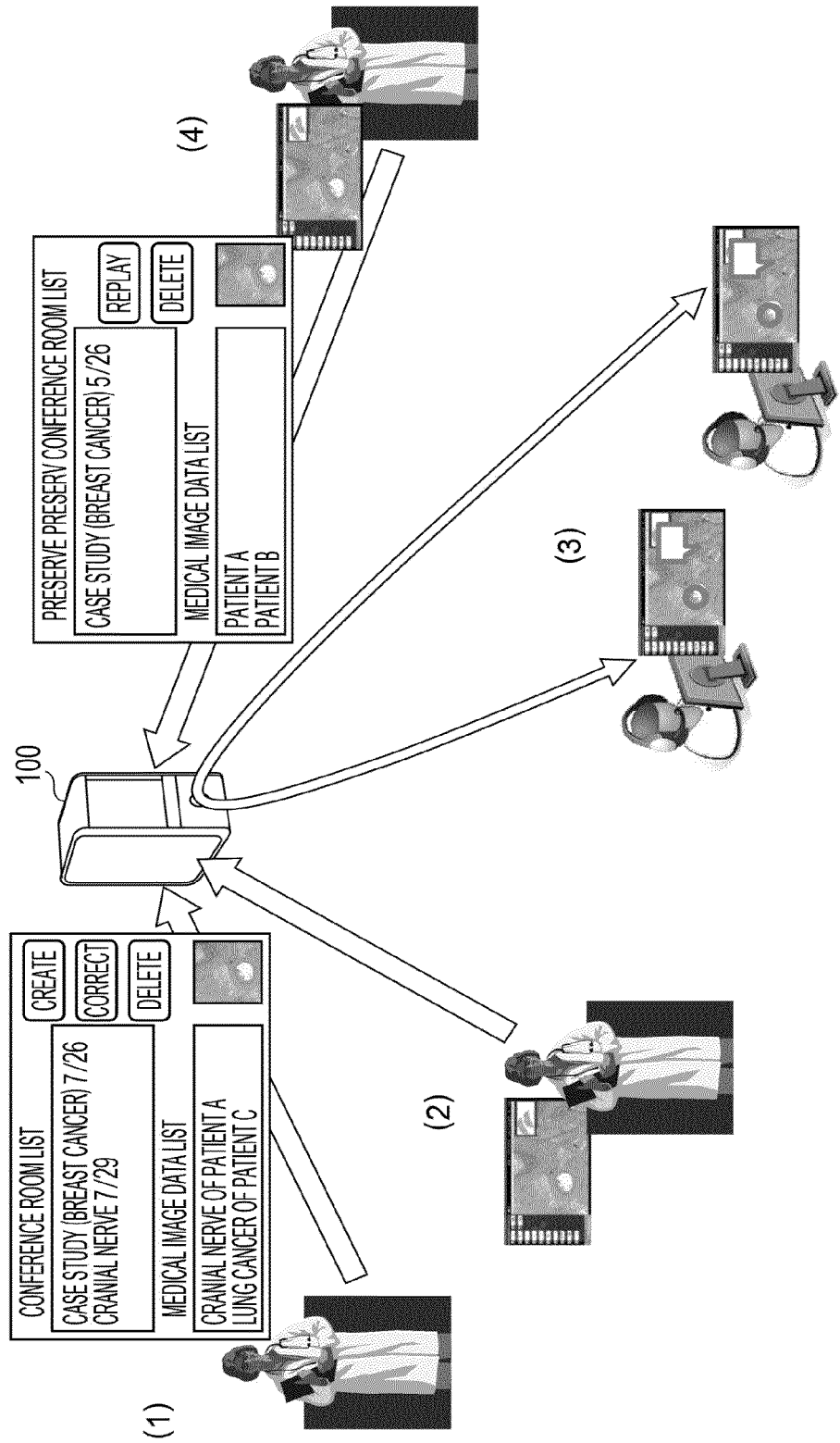
FIG. 4 is a diagram schematically illustrating main actions which a user of a client terminal can perform based on a conference room created in a medical image delivery server.

FIG. 4 schematically shows main actions which the users of the client terminals 200-1 to 200-N can perform based on the conference room created in the medical image delivery server 100 as described above. In other words, (1) when the conference room is in a conference scheduled state, the users can know that the conference is being held with the corresponding terminals. (2) When the conference room is in a conference scheduled state, the users can display and prepare for medical image data on the viewers of the corresponding client terminals. (3) When the conference room is in a conference live state, the users joining the conference room hold a network conference. (4) When the conference room is in a conference stored state, the users can replay (reproduce) the closed conference based on held operation history data.

Functions Regarding Conference included in Medical Image Delivery Server

Figure 5:
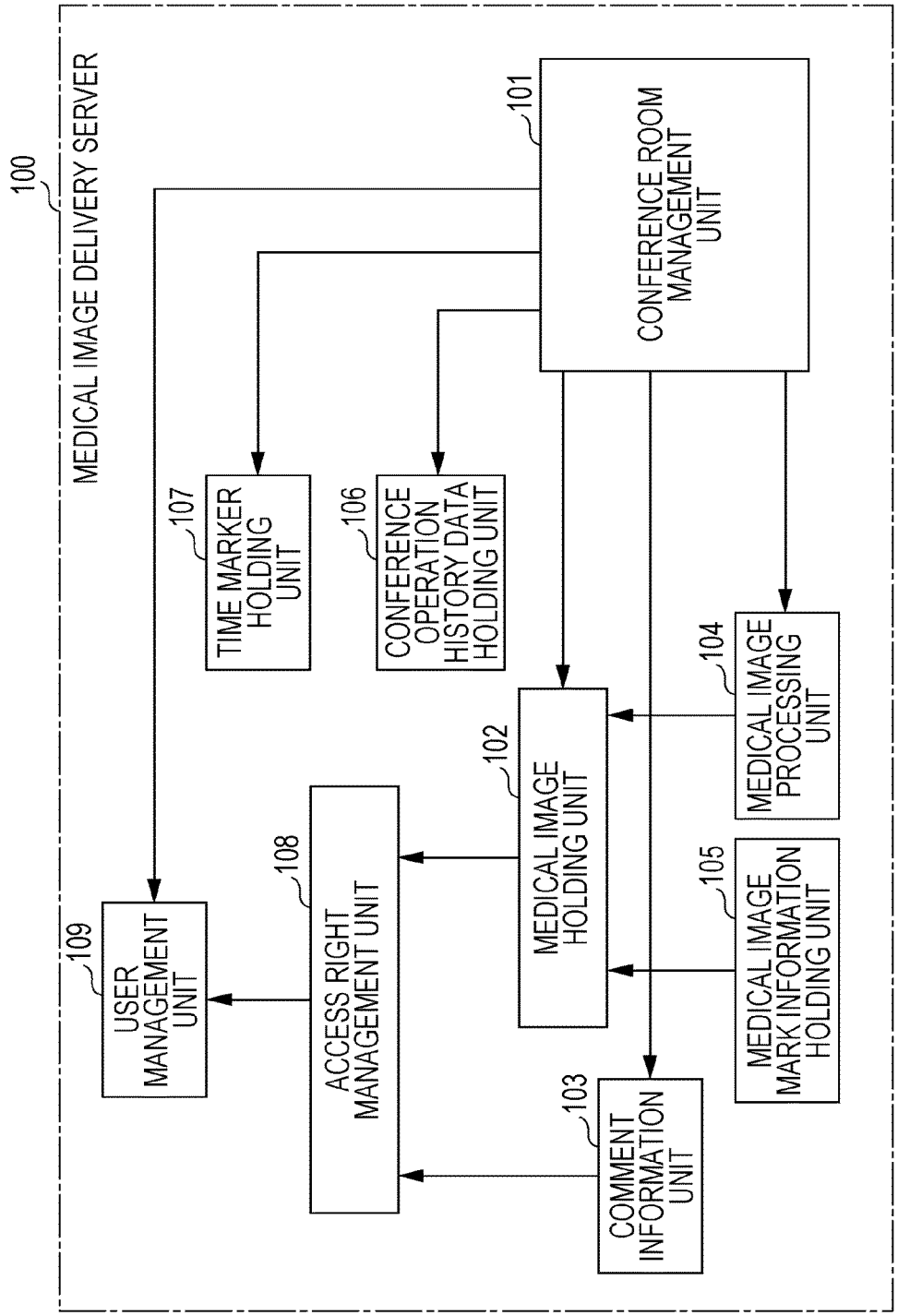
FIG. 5 is a functional block diagram illustrating functions regarding a conference which the medical image delivery server has.

FIG. 5 shows functions regarding a conference included in the medical image delivery server 100. The medical image delivery server 100 includes a conference room management unit 101, a medical image holding unit 102, a comment information holding unit 103, a medical image processing unit 104, and a medical image mark information holding unit 105. In addition, the medical image delivery server 100 includes a conference operation history data holding unit 106, a time marker holding unit 107, an access right management unit 108, and a user management unit 109.

Figure 6:
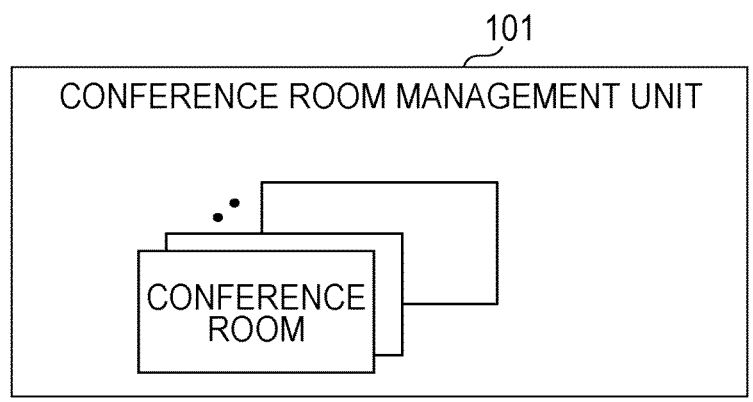
FIG. 6 is a diagram illustrating a case where a conference room management unit can hold a plurality of conference rooms.

The conference room management unit 101 processes commands such as a conference room generation command, a conference start commands, and a conference closing command from the client terminal. The conference room management unit 101 creates a conference room in response to the conference room generation command, and manages states of the conference room. FIG. 6 shows a case where the conference room management unit 101 can manage a plurality of conference rooms. Each conference room is correlated with medical image data discussed in the conference, comment information linked to the conference, and conference operation history data.

As described above, the conference room state includes a conference scheduled state, a conference live state, and a conference stored state (refer to FIG. 2). In a step where the conference room is created, the conference room is in a conference scheduled state. The conference room management unit 101 transitions the conference room from a conference scheduled state to a conference live state in response to a conference start command.

Further, the conference room management unit 101 transitions the conference room from a conference live state to the conference stored state in response to a conference closing operation. In addition, the conference room management unit 101 transitions the conference room from a conference stored state to a conference scheduled state in response to a conference resuming command.

The medical image holding unit 102 holds the predetermined number of medical image data including medical image data correlated with the conference. When a client terminal accesses predetermined medical image data, the medical image holding unit 102 asks the access right management unit 108 if a user of the client terminal has an access right. The medical image holding unit 102 permits the user to access the corresponding predetermined medical image data if the user has the access right.

For example, users joining a predetermined conference room (conference) have an access right to medical image data linked to the conference room created in the conference room management unit 101. Thereby, the joining users can access the corresponding medical image data, display a medical image on the viewers of the client terminals, and prepare for the conference.

The comment information holding unit 103 holds comment information given to medical image data. Here, the comment information is information such as arrow marks, flags, and freehand figures, which are given to arbitrary parts in a medical image by a user. The user can give comment information to medical image data not only in a conference live state but also, at other times, for example, in a conference scheduled state. The comment information holding unit 103 holds comment information given to medical image data in a conference live state so as to be correlated with the conference, and thus differentiates it from comment information given at other times.

When a client terminal accesses predetermined medical image data, the comment information holding unit 103 asks the access right management unit 108 if a user of the client terminal has an access right to each piece of comment information given to the medical image data. The comment information holding unit 103 permits the user to access only comment information to which the user has an access right. That is to say, in this case, only comment information to which the user of the client terminal has the access right is displayed on the medical image displayed on the viewer of the client terminal in an overlapping manner. For example, comment information given in a conference live state is displayed to all the users, but comment information given at other times is displayed to specific users.

The medical image processing unit 104 processes medical image data held in the medical image holding unit 102 such that the client terminals smoothly inspect medical images. For example, this process is compression of data. Through the data compression, the client terminals can smoothly inspect medical images because of the reduced communication amount during data transmission. In addition, for example, the process is encoding of data. Through the data encoding, the client terminals can smoothly inspect medical images because delay caused by encoding during data transmission can be removed.

Further, for example, the process is a change in data arrangement. In the data arrangement change, arrangement of medical image data is changed in terms of the storage order such as, for example, a "Hilbert order", and is held in an HDD (Hard Disk Drive) forming the medical image holding unit 102. Thereby, the client terminals can smoothly inspect medical images by reading the medical image data from the HDD at high speed.

Moreover, for example, the process is to copy or move medical image data to a storage medium which performs reading at high speed. For example, the medical image holding unit 102 includes an SSD (Solid State Drive) in addition to the above-described HDD as a storage medium, and copies or moves the medical image data held in the HDD to the SSD. The SSD has a characteristic data reading speed higher than the data reading speed of the HDD. Thereby, for example, since the medical image holding unit 102 reads accessed medical image data at high speed and delivers the data to the client terminals when the client terminals access the data, the client terminals can smoothly inspect medical images.

The medical image processing unit 104 preferentially processes medical image data which is scheduled to be used in a conference. As described above, each conference room managed by the conference room management unit 101 is correlated with medical image data discussed in the conference. The medical image processing unit 104 receives information for medical image data which is scheduled to be used in a conference, from, for example, the conference room management unit 101. As such, by preferentially processing the medical image data which is scheduled to be used in the conference, the client terminals can smoothly inspect medical images by the medical image data which is scheduled to be used in the conference.

For example, the medical image data which is scheduled to be used in the conference is copied to the SSD from the HDD in the medical image holding unit 102 in advance. In this case, during the conference, the medical image data used in the conference is delivered to the respective client terminals from the medical image delivery server at high speed. Therefore, the respective clients can smoothly inspect the medical images.

Figure 7:
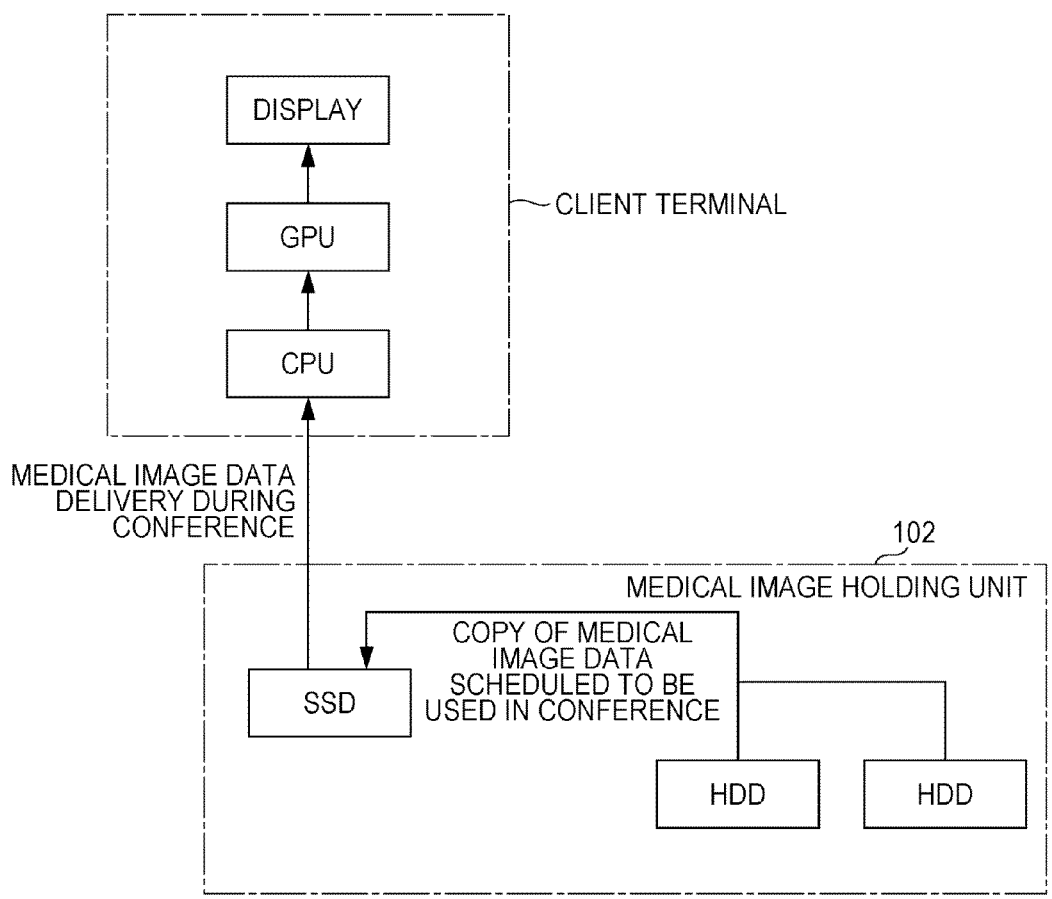
FIG. 7 is a block diagram schematically illustrating a data delivery system during conference.

FIG. 7 schematically shows a data delivery system during the conference. In the medical image holding unit 102 of the medical image delivery server 100, medical image data which is scheduled to be used in the conference is copied or moved from the HDD to the SSD in advance, for example, when the conference room is generated. During the conference, the medical image holding unit 102 reads the medical image data from the SSD so as to be delivered to each client terminal. Unless the SSD is defragmented, the high speed gradually disappears according to its use. Therefore, it is preferable that the high speed be maintained by performing the defragmentation after the conference is closed.

The medical image mark information holding unit 105 holds mark information which is selectively given to the medical image data which is held in the medical image holding unit 102. The user can upload medical image data to be held in the medical image holding unit 102, from the client terminal to the medical image delivery server 100. At this time, for example, the user may give mark information for identifying that effect, the disease name, and the like, to medical image data which is desired to be treated in a conference in a difficult case. As such, since the medical image mark information holding unit 105 holds the mark information, for example, it is possible to easily search for necessary medical image data by narrowing down image data using the mark information.

The conference operation history data holding unit 106 holds operation history data in a conference live state. As described above, the conference room managed by the conference room management unit 101 is transitioned from a conference live state to a conference stored state in response to the conference closing operation. Thereby, the conference operation history data holding unit 106 has overall conference operation history data related to the closed conference room. The conference operation history data holding unit 106 holds the operation history data in a conference live state, and thus it is possible to replay (reproduce) the entire conference using the held conference operation history data after the conference is closed.

As described above, the conference room managed by the conference room management unit 101 is transitioned from a conference stored state to a conference scheduled state in response to the resuming operation. Therefore, it is possible to resume the closed conference. In this case, the conference operation history data holding unit 106 holds the following as operation history data in a conference live state of the resumed conference.

In other words, the conference operation history data holding unit 106 holds operation history data obtained by adding operation history data of the resumed conference to copy data of the operation history data of the closed conference as the operation history data. In this case, the operation history data of the closed conference remains in the conference operation history data holding unit 106, and thus only the closed conference may be replayed (reproduced) singly. In addition, the operation history data of the resumed conference includes the operation history data of the closed conference, and thus continuous replay (reproduction) including the closed conference may be performed.

The time marker holding unit 107 holds a time marker indicating a remarkable point on the time axis given to a conference. Here, the time marker includes a first time marker given during a conference, and a second time marker given during a replay of the conference. The time marker holding unit 107 holds the first time marker and the second time marker so as to be differentiated from each other. As such, since the time marker holding unit 107 holds the time markers, a user can grasp the remarkable point of the conference on the time axis during the replay of the conference.

Figure 8:
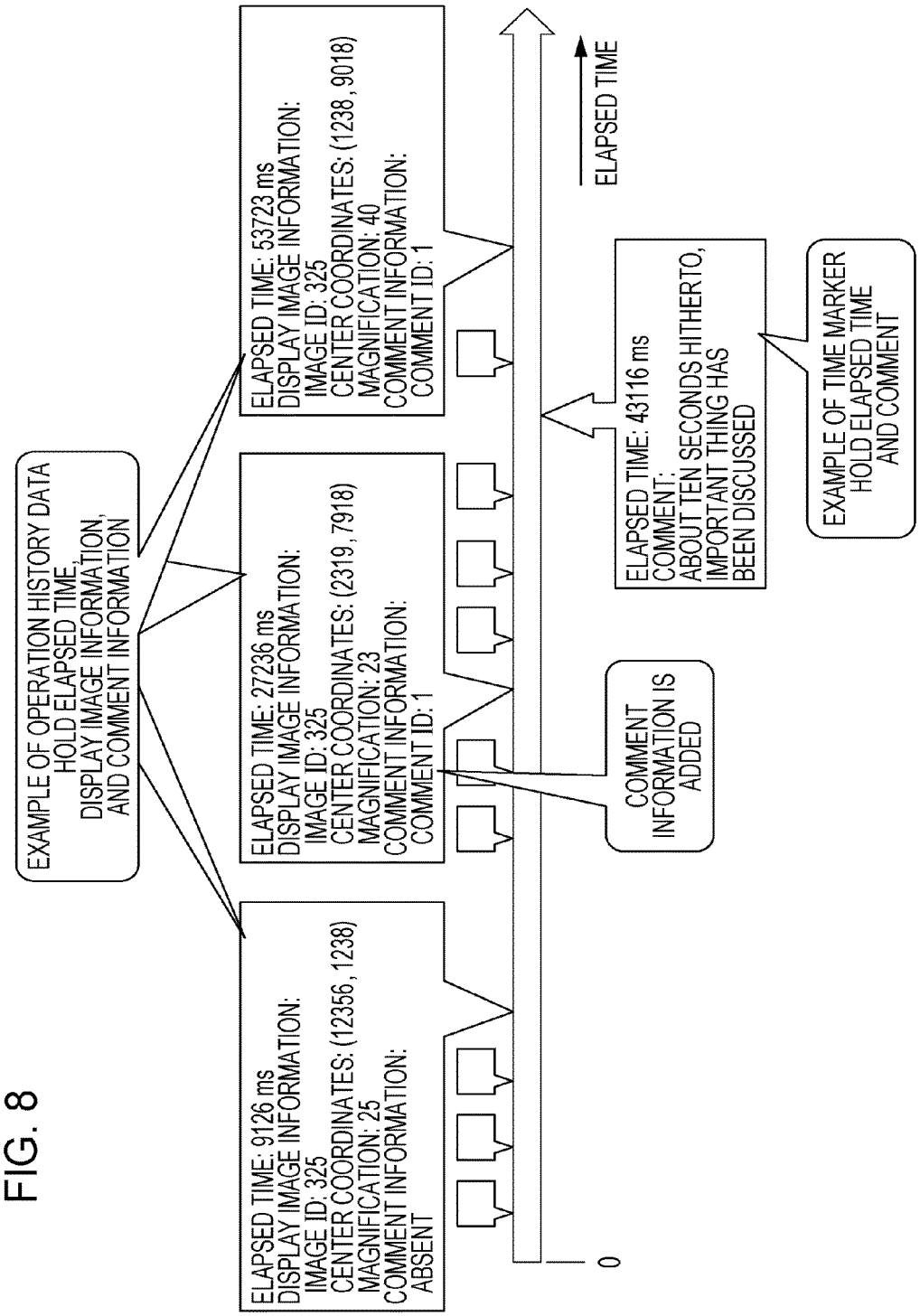
FIG. 8 is a diagram illustrating an example of the conference operation history data and a time marker.

FIG. 8 shows an example of the operation history data and the time marker. The operation history data includes operation data at the respective time points when there are changes in the magnification of a medical image or a central position, addition of comment information to the medical image, and the like, correlated with the elapsed time during the conference. In addition, the time marker is formed by data including, for example, comments correlated with the elapsed time during conference.

The access right management unit 108 manages information as to which user is allowed to access the medical image data, the comment information, the conference room, and the like. The user management unit 109 manages user information.

Conference Scheduled State

Figure 9:
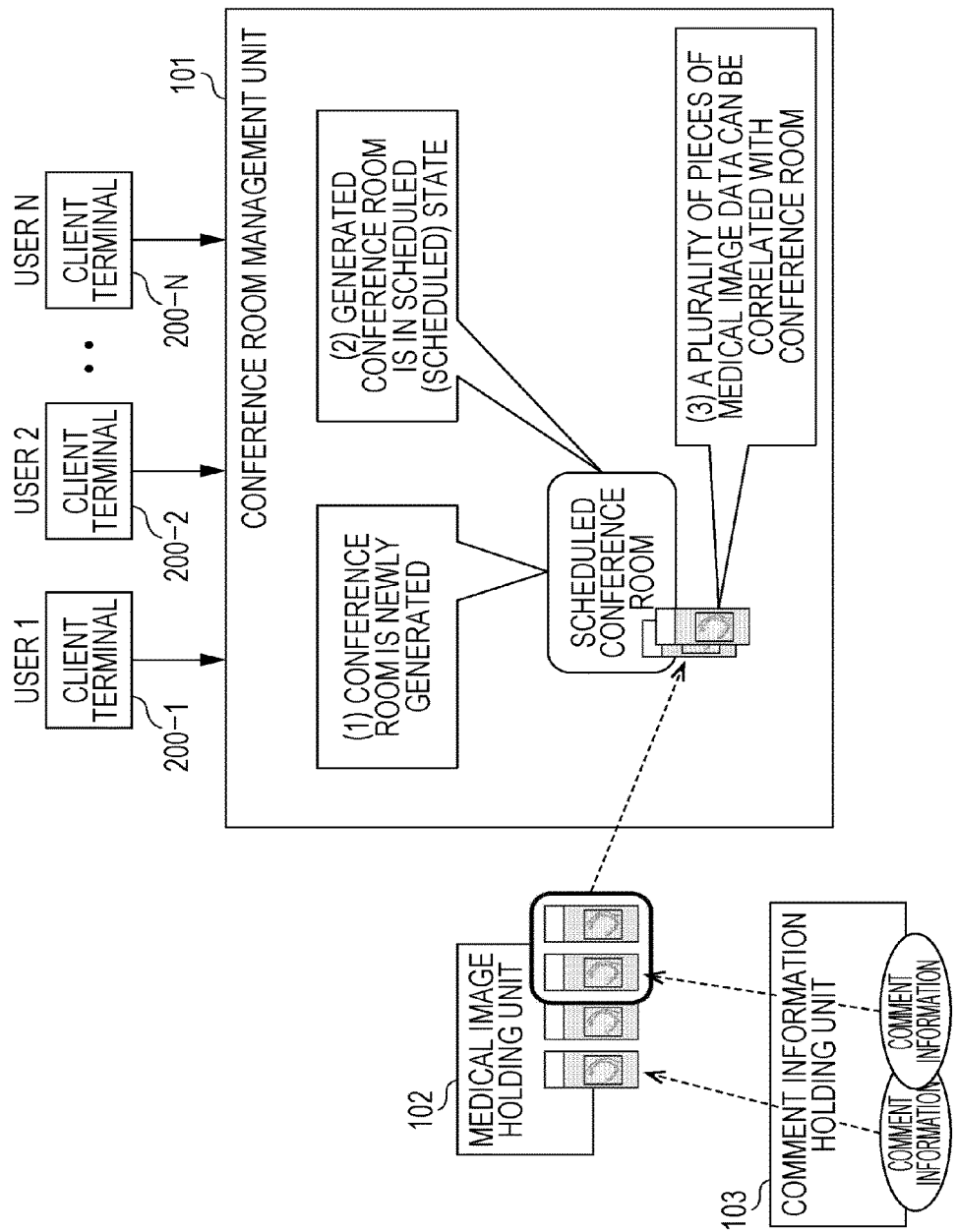
FIG. 9 is a diagram illustrating a scheduled state of a conference room.

The scheduled state of the conference room will be further described with reference to FIG. 9. A conference room is newly generated in the conference room management unit 101 through an operation from a client terminal of a user. The conference room is in a conference scheduled state in the generated step. When the conference room is generated, medical image data to be used in the conference among the predetermined number of medical image data held in the medical image holding unit 102 is correlated with the conference room.

Figure 10:
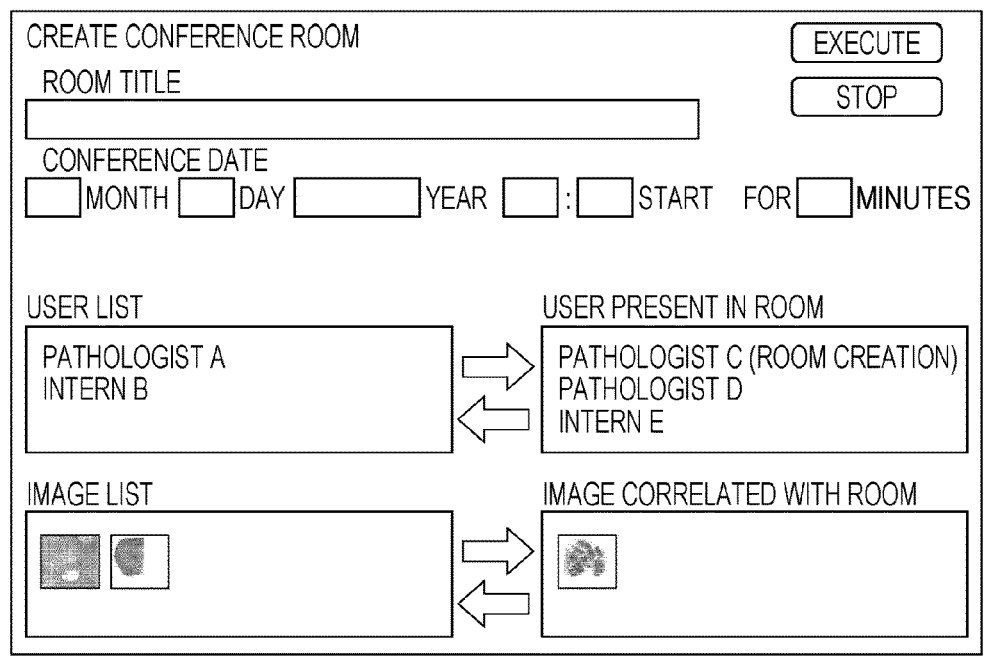
FIG. 10 is a diagram illustrating an example of the conference room creation GUI displayed on a viewer of a client terminal when a conference room is created.

FIG. 10 shows an example of the conference room creation GUI (Graphical User Interface) displayed on the viewer of the client terminal when the conference room is generated. The user creates a conference room based on the GUI. The user inputs a "room tile" and "conference date".

In addition, the user may select users joining the room from a "user list". The users displayed in "user list" are, for example, users managed by the above-described user management unit 109 of the medical image delivery server 100. The selected users (including a room creator) are displayed in the column "user present in room". Users can be simply moved through a drag operation between the column "user list" and the column "user present in room". In addition, in the shown example, a user moved to the column "user present in room" is excluded from the "user list", but may remain in the "user list".

In addition, the user may select medical images (medical image data) used in the conference room from an "image list". The medical images (thumbnails) displayed in the "image list" are, for example, images of the medical image data held in the above-described medical image holding unit 102 of the medical image delivery server 100. In this case, an image to which mark information is given may be displayed so as to be differentiated from other images based on the mark information held in the medical image mark information holding unit 105. Alternatively, in this case, only an image to which specific mark information is given may be displayed.

A medical image selected as a medical image used in the conference room is displayed in a column "image correlated with room". An image can be simply moved through a drag operation between the column "image list" and the column "image correlated with room". In addition, in the shown example, a medical image moved to the column "image correlated with room" is excluded from the "image list" but may remain in the "image list".

When the user clicks the "execute" button after performing the above-described input and selection, a conference room is generated in the conference room management unit 101 of the medical image delivery server 100. At this time, a user moved to the column "user present in room" can access the conference room, medical image data used in the conference, and the like. That is to say, the access right management unit 108 of the medical image delivery server 100 automatically updates an access right. In addition, when the user clicks the "stop" button, the conference room stops being generated.

Figure 11:
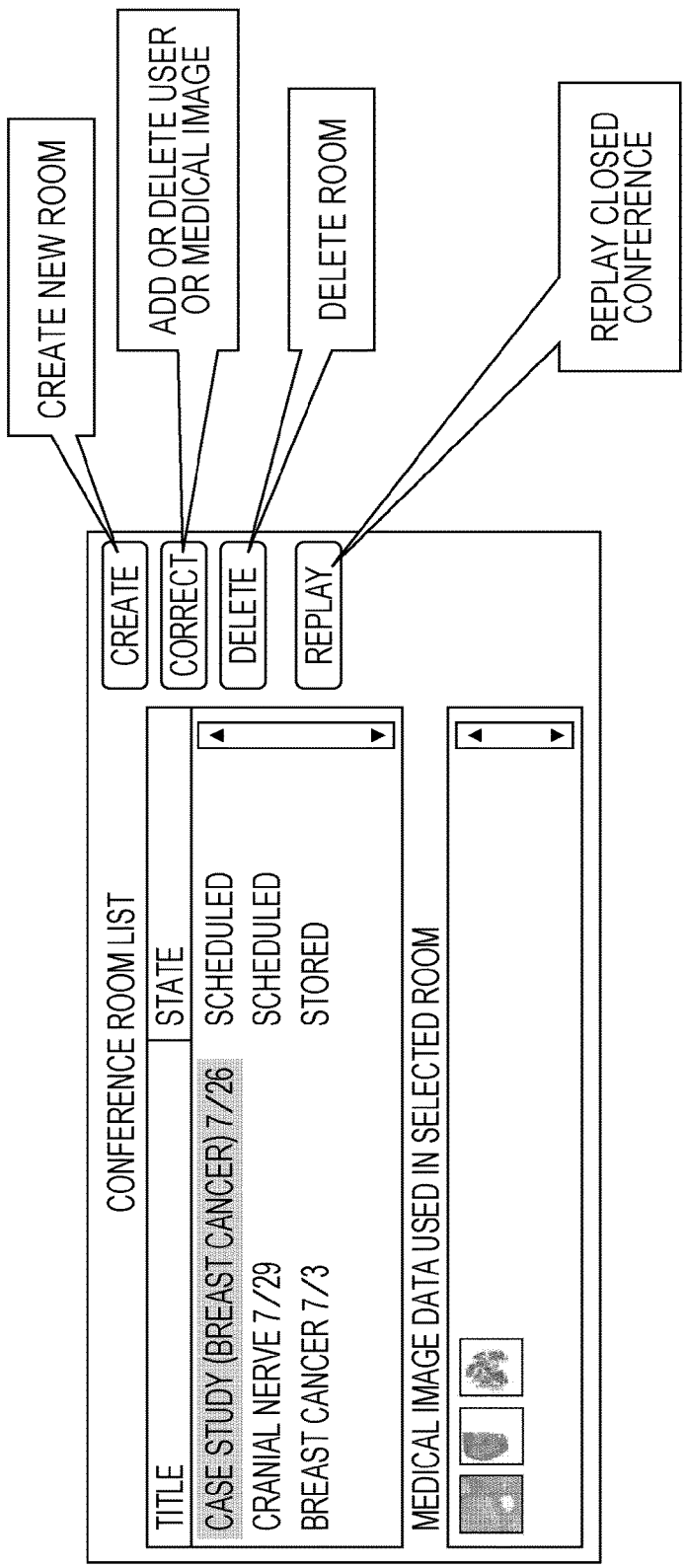
FIG. 11 is a diagram illustrating an example where a client terminal accesses a medical image delivery server and a GUI for conference room list display is displayed on a viewer thereof.

FIG. 11 shows an example where a client terminal accesses the medical image delivery server 100 and the GUI for conference room list display is displayed on the viewer thereof.

The GUI displays titles and conference date of the conference rooms managed by the conference room management unit 101 of the medical image delivery server 100 in a list view. All the medical images (thumbnails) used in the conference rooms selected on the GUI are displayed in the column "medical image data used in selected room" in a list view. In addition, the conference rooms displayed in a list view are in one of the scheduled state, the live state, and the stored state, and the state is also displayed. In addition, in the shown example, the conference room having the title of "case study (breast cancer) 7/26" is in a selected state.

In the GUI example shown in FIG. 11, a new conference room may be created by clicking the "create" button. At this time, the viewer of the client terminal displays the conference room creation GUI as shown in FIG. 10 described above, and the user can create a new conference room. In addition, in the GUI example shown in FIG. 11, a user or a medical image may be added to or deleted from the selected conference room by clicking the "correct" button.

Further, in the GUI example shown in FIG. 11, the selected conference room can be deleted by clicking the "delete" button. In addition, in the GUI example shown in FIG. 11, a closed conference is replayed (reproduced) by selecting the conference room in a stored state and clicking the "replay" button. In this case, images of a closed conference which are displayed on the viewer of the client terminal are sequentially changed with the passage of time in the same manner as the images displayed during the conference. In addition, the sound output from a sound output unit of the client terminal also flows with the passage of time in the same manner as the sound output during the conference.

Figure 12:
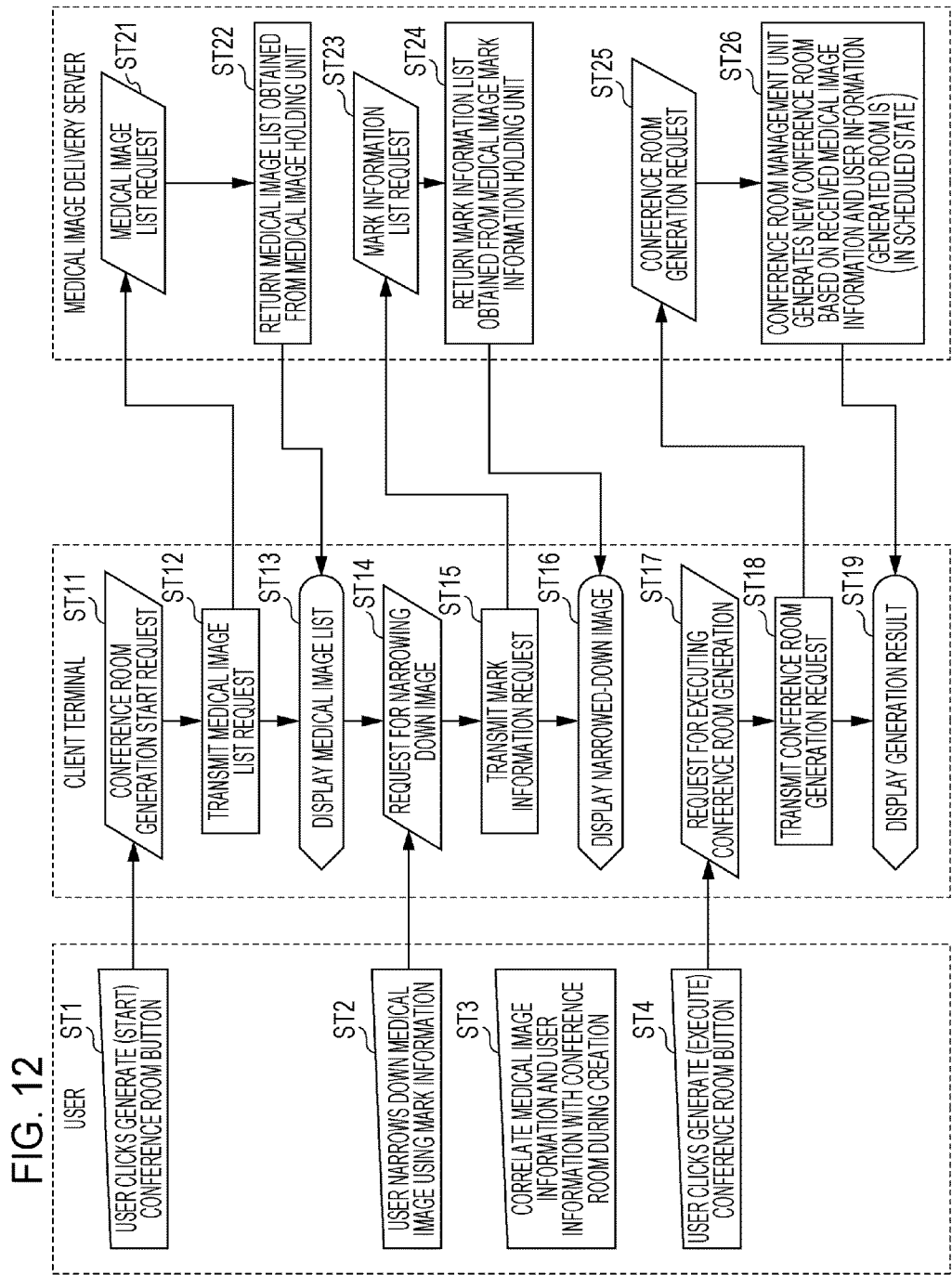
FIG. 12 is a diagram illustrating an example of the process flow in a user, a client terminal, and a medical image delivery server when a conference room is generated.

The flowchart in FIG. 12 shows an example of the process flow in the user, the client terminal, and the medical image delivery server 100 when the conference room is generated. In step ST1, the user clicks the "create" button on the GUI for conference room list display (refer to FIG. 11). The client terminal enters a conference room generation start request in step ST11, and transmits a medical image list request to the medical image delivery server 100 in step ST12.

If receiving the medical image list request from the client terminal in step ST21, the medical image delivery server 100 returns the medical image list obtained from the medical image holding unit 102 to the client terminal in step ST22. If receiving the medical image list from the medical image delivery server 100, the client terminal displays the medical image list on the viewer in step ST13. In this case, the viewer displays the conference room creation GUI (Graphical User Interface) where medical images (thumbnails) are displayed in the column "image list" in a list view, as shown in FIG. 10.

Next, the user narrows down the medical images using mark information in step ST2. At this time, the user inputs narrowing-down information such as a disease name. The client terminal enters a narrowing-down request state in step ST14, and transmits a mark information list request including the narrowing-down information to the medical image delivery server 100 in step ST15.

The medical image delivery server 100 receives the mark information list request from the client terminal in step ST23. In step ST24, the medical image delivery server 100 obtains a list (mark information list) of medical image data matching the narrowing-down information included in the mark information list request from the medical image mark information holding unit 105, and returns the list to the client terminal. In step ST15, if receiving the mark information list from the medical image delivery server 100, the client terminal displays the narrowed-down image based on the mark information list. In other words, only the medical images matching the medical image narrowing-down of the user are displayed as medical images (thumbnails) displayed in the column "image list" of the above-described conference room creation GUI.

Next, in step ST3, the user correlates the conference room during creation with medical image information and user information on the conference room creation GUI. That is to say, in the conference room creation GUI, users who can be included in the column "user present in room" are selected from the user list, and images which can be included in the column "image correlated with room" are selected from the image list.

Thereafter, in step ST4, the user instructs to generate a conference room by clicking the "execute" button on the conference room creation GUI. The client terminal enters a conference room generation executing state in step ST17. In addition, in step ST18, the client terminal transmits a conference room generation request including medical image information and user information in addition to information for the room title and conference date input on the conference room creation GUI, to the medical image delivery server 100.

In step ST25, the medical image delivery server 100 receives the conference room generation request from the client terminal. Further, in step ST26, the conference room management unit 101 generates and manages a new conference room based on the information for the room title and conference date, the medical image information, and the user information. In step ST19, the client terminal displays a generated result according to the generation of the new conference room. For example, a GUI for conference room list display to which the new conference room is added is displayed on the viewer (refer to FIG. 11).

Figure 13:
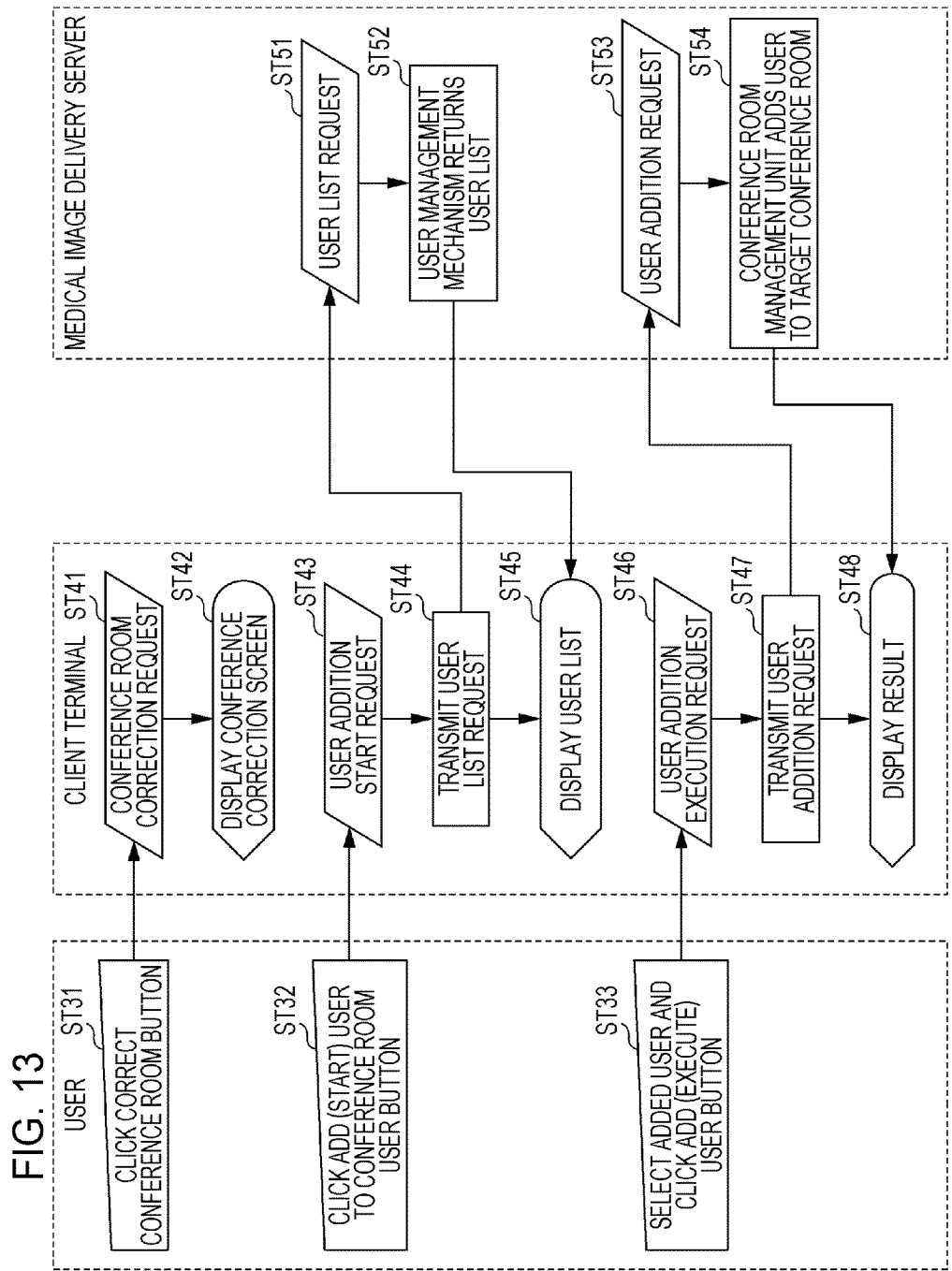
FIG. 13 is a diagram illustrating an example of the process flow in a user, a client terminal, and a medical image delivery server when a user is added to a conference room.

The flowchart in FIG. 13 shows an example of the process flow in the user, the client terminal, and the medical image delivery server 100 when a user is added to the conference room. In step ST31, the user clicks the "correct" button on the GUI for conference room list display (refer to FIG. 11). In response thereto, the client terminal enters a conference room correction request state in step ST41, and displays a conference room correction screen (not shown) on the viewer in step ST42.

Next, the user clicks an "add user" button present on the conference room correction screen in step ST32. The client terminal enters a user addition start request state in step ST43, and transmits a user list request to the medical image delivery server 100 in step ST44. If the user list request is received in step ST51, the medical image delivery server 100 returns the user list managed by the user management unit 109 to the client terminal in step ST52. In step ST45, the client terminal displays the user list on the viewer based on the received user list.

Thereafter, the user selects a user (a plurality of users may be selected) to be added from the user list, and clicks an "add (execute) user" button in step ST33. The client terminal enters a user addition executing request state in step ST46, and transmits a user addition request including information for the added user to the medical image delivery server 100 in step ST47. In step ST53, the medical image delivery server 100 receives the user addition request. In addition, the conference room management unit 101 adds the user to the target conference room in step ST54. In response to the addition of the user, in step ST48, the client terminal displays a result of the user addition, that is, displays that the user addition to the target conference room is normally performed, and the like.

Conference Live State

Figure 14:
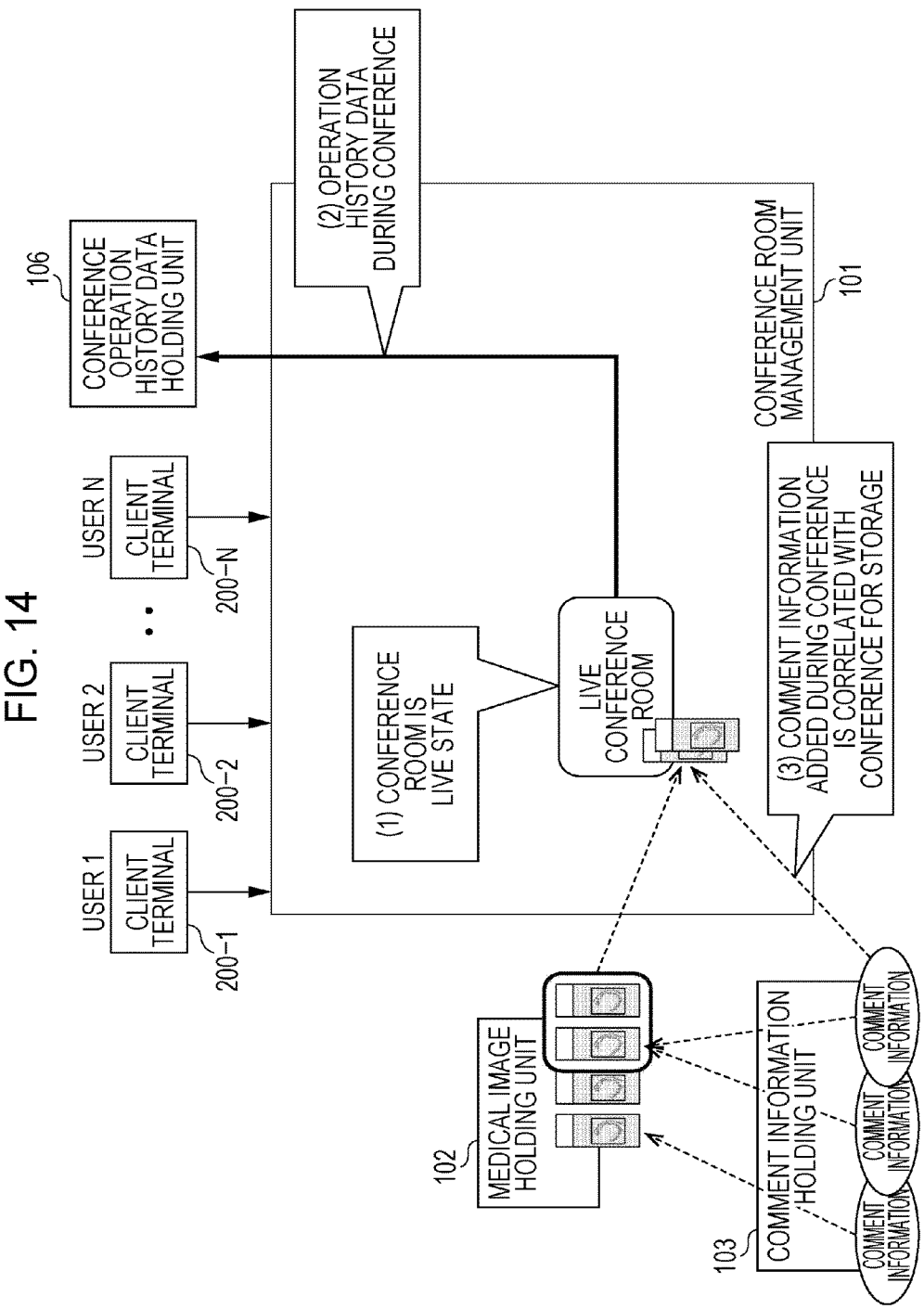
FIG. 14 is a diagram illustrating a live state of a conference room.

The conference live state will be further described with reference to FIG. 14. The conference room created in the medical image delivery server 100 is transitioned from a conference scheduled state to a conference live state by the starting operation from the client terminal of the user. The conference operation history data holding unit 106 preserves operation history data of a conference which is being held. Comment information given to medical image data by the user during the conference is correlated with the conference and is stored in the comment information holding unit 103.

Figure 15:
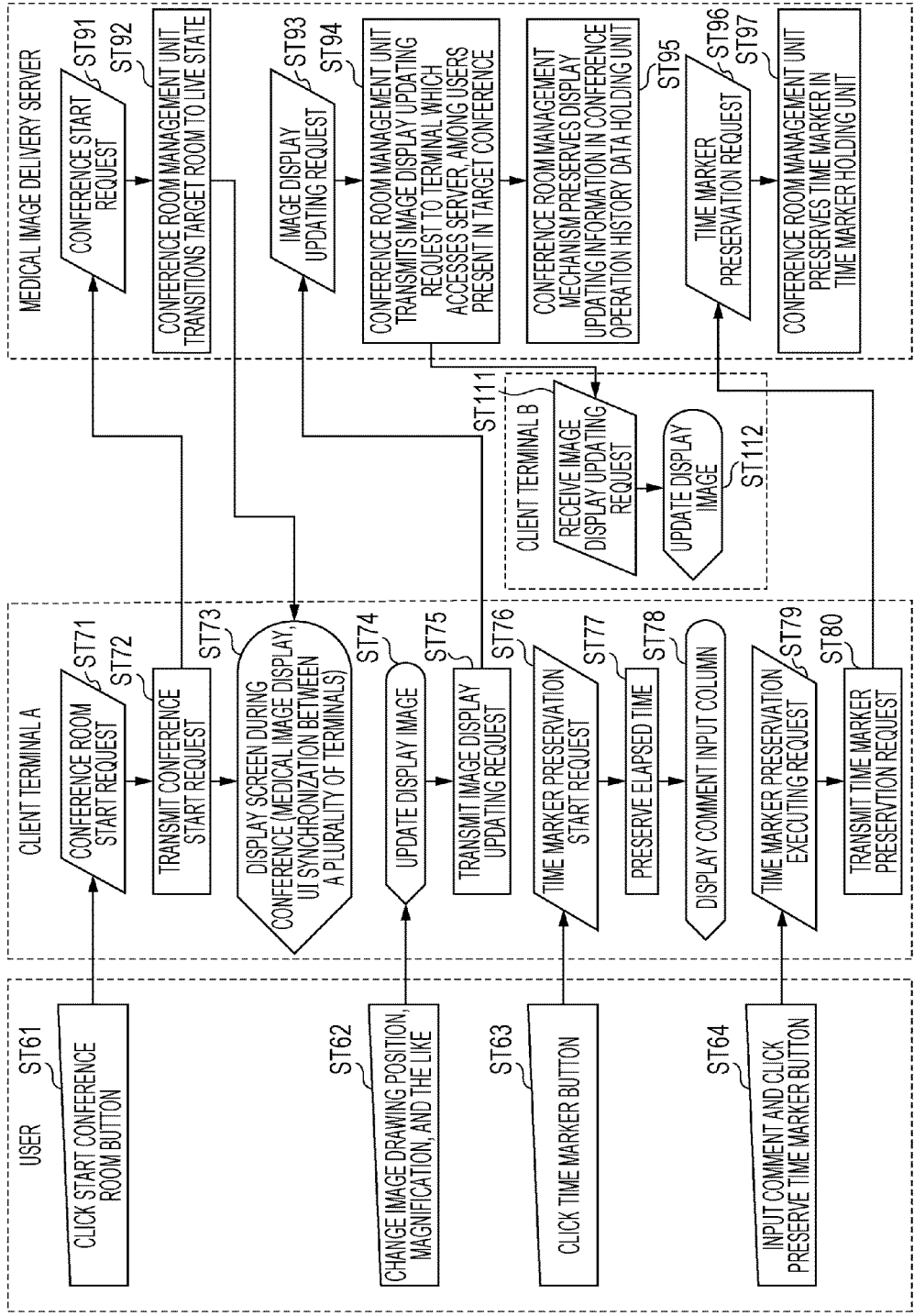
FIG. 15 is a flowchart (1/2) illustrating an example of the process flow in a user, a client terminal, and a medical image delivery server when a conference room is in a live state.
Figure 16:
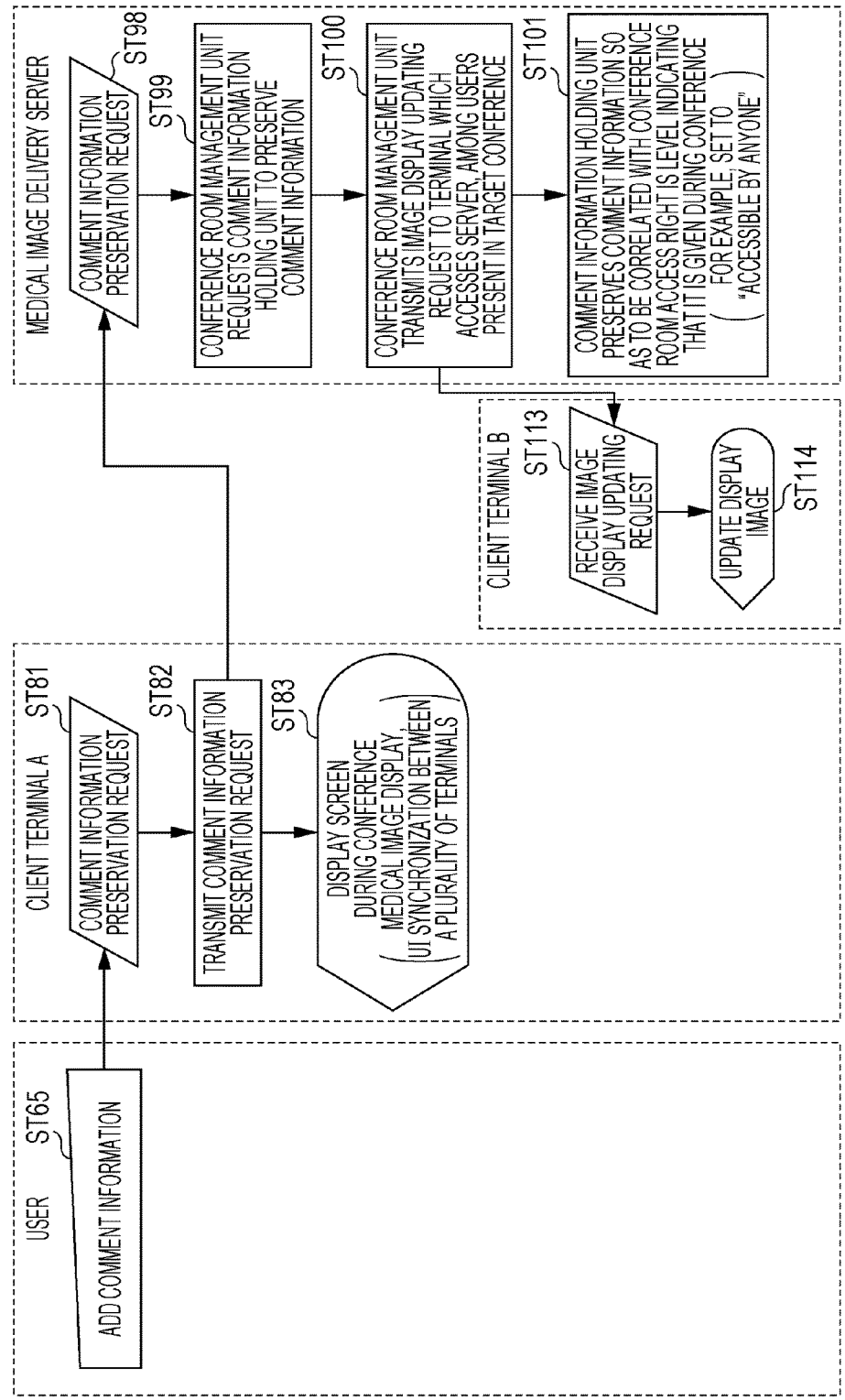
FIG. 16 is a flowchart (2/2) illustrating an example of the process flow in a user, a client terminal, and a medical image delivery server when a conference room is in a live state.

The flowcharts in FIGS. 15 and 16 show an example of the process flow in the user, the client terminal, and the medical image delivery server 100 in a conference live state. In step ST61, the user accesses the target conference room in a scheduled state, and clicks the "start button" on a display screen of the viewer of the client terminal. The client terminal (client terminal A) enters a conference room start request state in step ST71, and transmits a conference start request including information for a target conference room to the medical image delivery server 100 in step ST72.

In step ST91, the medical image delivery server 100 receives the conference start request from the client terminal. In step ST92, the conference room management unit 101 transitions the target conference room state from a conference scheduled state to the conference live state. In response thereto, the client terminal displays a screen in a conference live state on the viewer in step ST73. Medical images are displayed on the screen, and UI (User Interface) operations in a plurality of client terminals joining the target conference room are synchronized with each other. That is to say, a screen operation or comment information is synchronized and thus the same display is performed in the respective client terminals.

Next, in step ST62, the user changes image drawing positions, magnifications, and the like. In response to the change operation, the client terminal updates the displayed image in step ST74. In addition, the client terminal transmits an image display updating request including updated content information to the medical image delivery server 100 in step ST75.

In step ST93, the medical image delivery server 100 receives the image display updating request. In step ST94, the conference room management unit 101 transmits the image display updating request including the updated content information to a client terminal B connected to the server among the client terminals of the users joining the target conference. In addition, the conference room management unit 101 preserves display updated information in the conference operation history data holding unit 106. The client terminal B receives the image display updating request in step ST111, and updates a display image in step ST112. Thereby, the display image of the client terminal B has the same display state as the display image of the client terminal A.

Next, in step ST64, the user inputs comments on the display screen of the viewer of the client terminal, and clicks a "preserve time marker" button. The client terminal enters a time marker preservation executing request state in step ST79, and transmits a time marker preservation request including the comment information to the medical image delivery server 100 in step ST80. In step ST96, the medical image delivery server 100 receives the time marker preservation request from the client terminal. In addition, the conference room management unit 101 preserves the comment-added time marker in the time marker holding unit 107.

Next, in step ST65, the user adds comment information to the medical image on the display screen of the viewer of the client terminal. The client terminal enters a comment information preservation request state in step ST81, and transmits a comment information preservation request including the comment information to the medical image delivery server 100 in step ST82. In addition, the client terminal displays the medical image to which the comment information is added, on the viewer in step ST83.

In step ST98, the medical image delivery server 100 receives the comment information preservation request from the client terminal. In step ST99, the conference room management unit 101 requests the comment information holding unit 103 to preserve the comment information. In addition, in step ST100, the conference room management unit 101 transmits an image display updating request including the updated content information to the client terminal B connected to the server among the client terminals of the users joining the target conference. The client terminal B receives the image display updating request in step ST113, and updates a display image in step ST114. Thereby, the display image of the client terminal B displays the comment information on the medical image in the same manner as the display image of the client terminal A.

In step ST101, the comment information holding unit 103 of the medical image delivery server 100 preserves the comment information so as to be correlated with the conference room. In this case, the comment information holding unit 103 sets an access right to the comment information to a level (for example, "accessible by anyone") which indicates that given during the conference.

Figure 17:
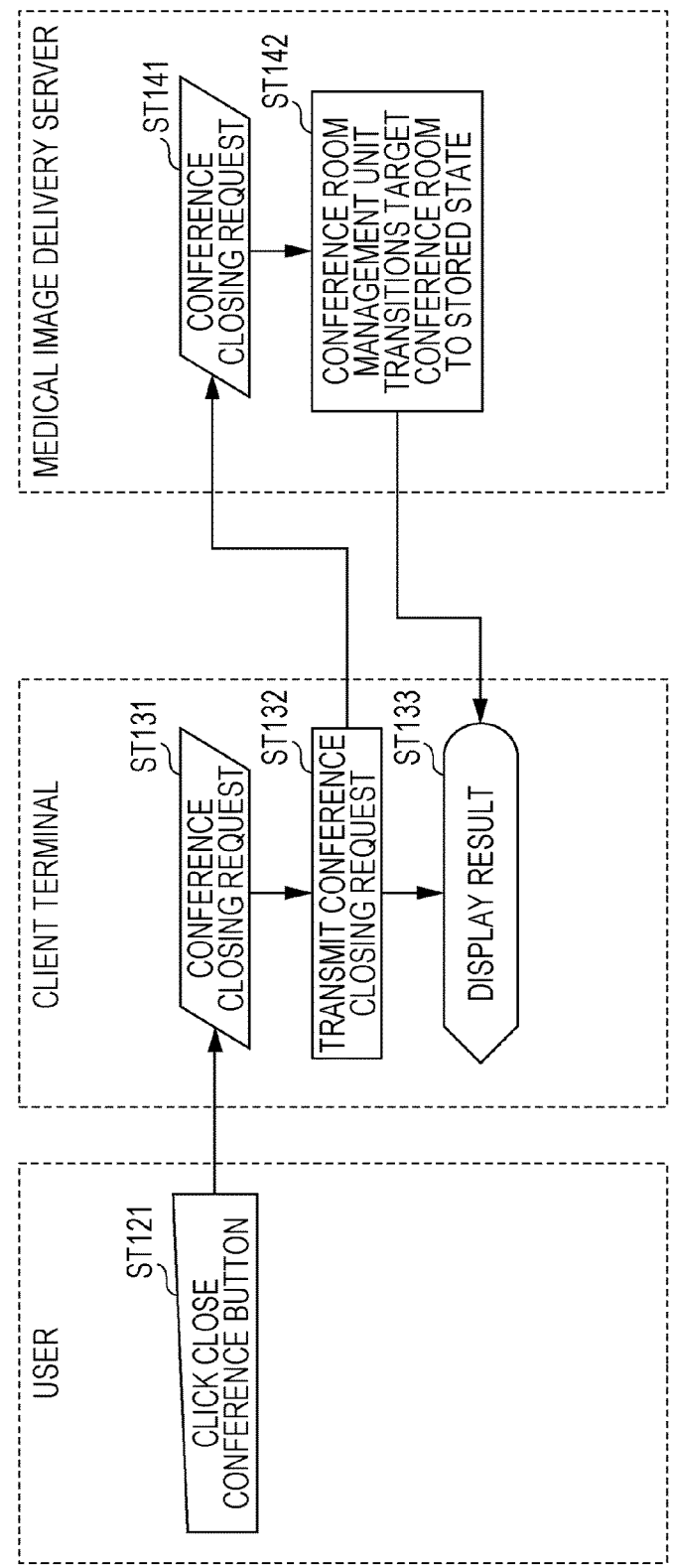
FIG. 17 is a diagram illustrating an example of the process flow in a user, a client terminal, and a medical image delivery server when a conference is closed.

The flowchart in FIG. 17 shows an example of the process flow in the user, the client terminal, and the medical image delivery server 100 when the conference is closed. In step ST121, the user clicks "close conference button" on the display screen of the viewer of the client terminal. The client terminal enters a conference closing request state in step ST131, and transmits a conference closing request to the medical image delivery server 100 in step ST132.

In step ST141, the medical image delivery server 100 receives the conference closing request. In step ST142, the conference room management unit 101 transitions the conference room state from a conference live state to a conference stored state. In response to the conference room state transition, the client terminal displays a result, that is, closing of the conference, in step ST133.

Conference Stored State

Figure 18:
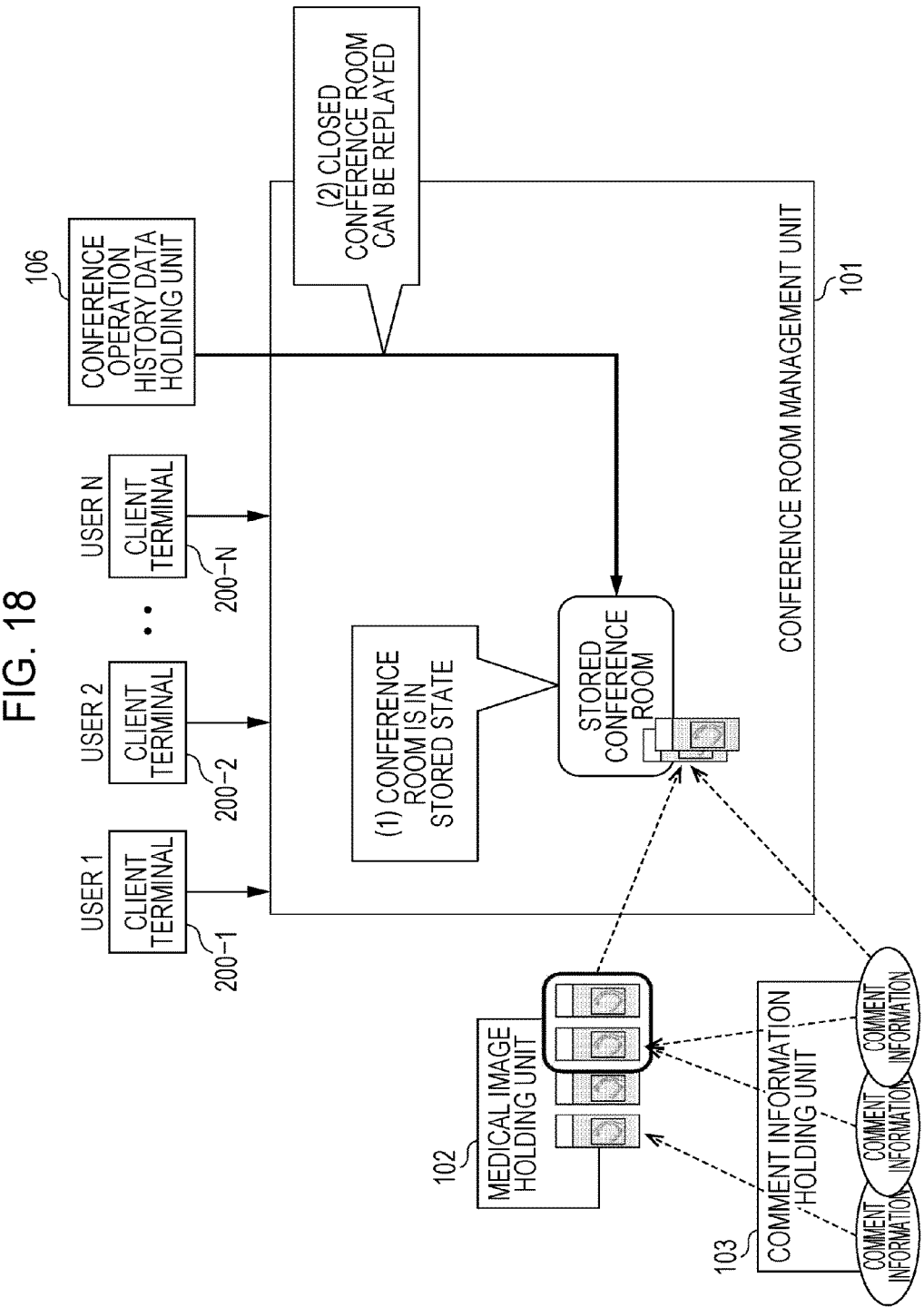
FIG. 18 is a diagram illustrating a stored state of a conference room.

The stored state of the conference room will be further described with respect to FIG. 18. The conference room in the medical image delivery server 100 is transitioned from a conference live state to a conference stored state in response to the closing operation from the client terminal of the user, as described above. In the conference stored state, it is possible to replay (reproduce) the conference based on the operation history data of the closed conference, held in the conference operation history data holding unit 106.

Figure 19:
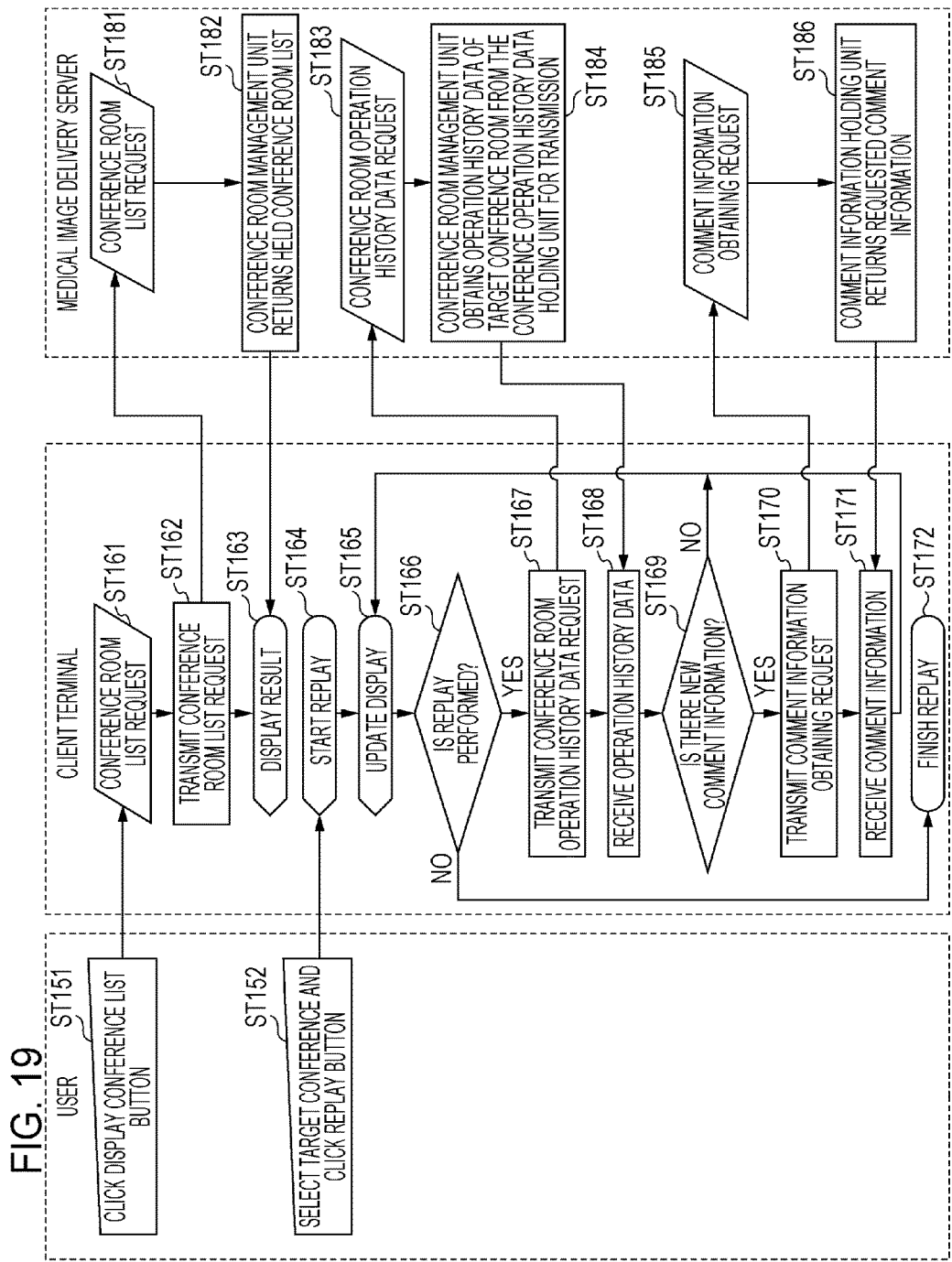
FIG. 19 is a diagram illustrating an example of the process flow in a user, a client terminal, and a medical image delivery server when a conference is replayed.

The flowchart in FIG. 19 shows an example of the process flow in the user, the client terminal, and the medical image delivery server 100 when the conference is replayed. In step ST151, the user clicks a "display conference list" button on the display screen of the viewer of the client terminal. The client terminal enters a conference room list request state in step ST161, and transmits a conference room list request to the medical image delivery server 100 in step ST162.

In step ST181, the medical image delivery server 100 receives the conference room list request from the client terminal. In step ST182, the conference room management unit 101 returns the held and managed conference room list to the client terminal. In step ST163, if receiving the conference room list from the medical image delivery server 100, the client terminal displays the conference room list on the viewer. In this case, for example, the GUI for conference room list display as shown in FIG. 11 is displayed on the viewer.

Next, in step ST152, the user selects a conference room to be replayed from the displayed conference room list, and clicks the "replay" button. In step ST164, the client terminal starts replaying the target conference. In addition, in step ST165, the client terminal updates the display image based on the operation history data obtained from the medical image delivery server 100.

Next, in step ST166, the client terminal determines whether or not replay is performed. If the replay is not performed, for example, if the user stops the replay, or if the replay is performed to the end, the client terminal finishes the replay in step ST172. On the other hand, when the replay is performed, the client terminal transmits a conference room operation history data request to the medical image delivery server 100 in step ST167.

In step ST183, the medical image delivery server 100 receives the conference room operation history data request. In step ST184, the conference room management unit 101 obtains operation history data for the target conference room from the conference operation history data holding unit 106 and transmits the data to the client terminal. In step ST168, the client terminal receives the operation history data sent from the medical image delivery server 100.

In step ST169, the client terminal determines whether or not there is new comment information. If there is no new comment information, the client terminal instantly returns to the process in step ST165. On the other hand, if there is new comment information, the client terminal transmits a comment information obtaining request to the medical image delivery server 100 in step ST170.

In step ST185, the medical image delivery server 100 receives the comment information obtaining request. In addition, in step ST186, the comment information holding unit 103 transmits the requested comment information to the client terminal. In step ST171, the client terminal receives the comment information sent from the medical image delivery server 100. In addition, the client terminal returns in order to perform the process in step ST165.

Figure 20:
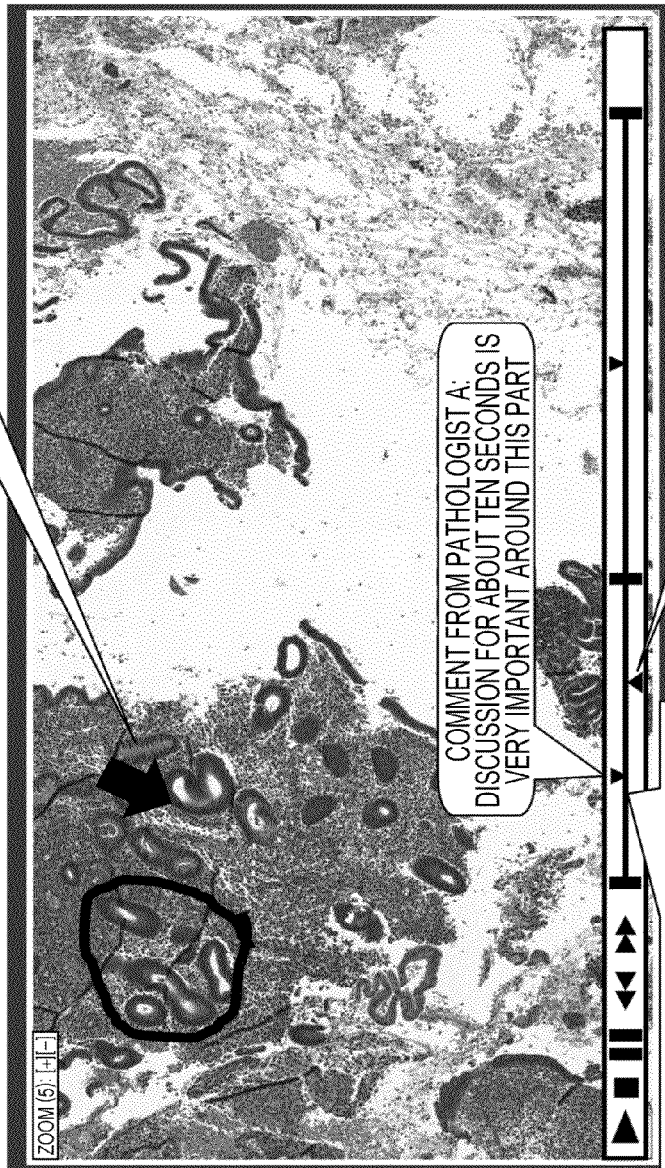
FIG. 20 is a diagram illustrating an example of the image (UI) displayed on a viewer when a conference is replayed.

FIG. 20 shows an example of the display image (UI) of the viewer when the conference is replayed. If comment information is given to the displayed medical image, the comment information is displayed on the medical image in an overlapping manner. In addition, on the lower part of the display screen, bars indicating buttons such as a play button, a pause button, a stop button, a fast forward button, a rewind button, and the like, operated by the user, are displayed. Further, a seek bar indicating which part of a serial conference is replayed is displayed on the bar, and a time marker is also displayed on the seek bar part.

As described above, the time markers include a time marker given during the conference, and a time marker given during the replay by a replayer. For example, the time marker given during the conference is displayed on the seek bar, and the time marker given during the replay is displayed under the seek bar. For example, if the user brings a mouse cursor into contact with the mark part, a comment given to the time marker is displayed as shown.

In addition, the user can delete any medical image data held in the medical image holding unit 102 of the medical image delivery server 100 by operating the client terminal. The flowchart in FIG. 21 shows an example of the process flow in the user, the client terminal, and the medical image delivery server 100 when the medical image is deleted. In step ST201, the user selects medical image data (medical image) to be deleted and clicks a "delete medical image" button on the display screen of the viewer of the client terminal. The client terminal enters a medical image deletion request state in step ST211, and transmits a medical image deletion request including information for the medical image to be deleted to the medical image delivery server 100 in step ST212.

In step S221, the medical image delivery server 100 receives the medical image deletion request from the client terminal. In step ST222, the medical image holding unit 102 asks the conference room management unit 101 if the medical image data to be deleted is correlated with the conference room. In addition, in step ST223, the medical image holding unit 102 determines whether or not the medical image data to be deleted is correlated with the conference room, based on the result of the enquiry in step ST222.

If the medical image data to be deleted is correlated with the conference room, the medical image holding unit 102 does not delete the medical image data which is requested to be deleted, but transmits an error or a warning message for confirming the deletion, to the client terminal, in step ST224. On the other hand, if the medical image data to be deleted is not correlated with the conference room, the medical image holding unit 102 deletes the medical image data which is requested to be deleted, and transmits a result thereof to the client terminal, in step ST225. In step ST213, the client terminal displays the result of the deletion request based on the transmission from the medical image delivery server 100.

As described above, in the network conference system 10 shown in FIG. 1, the conference room management unit 101 of the medical image delivery server 100 manages conference rooms for holding a conference. As a conference room state, there are one state which is a conference live state, and other states (conference scheduled state and conference stored state) different from the one state. Therefore, it is possible to realize a network conference system which is easily used according to a workflow of a doctor.

That is to say, since there is the conference scheduled state as a conference room state, an advance notice of the conference can be given, and a person who is scheduled to join the conference can inspect a medical image in advance and prepare for the conference. In addition, since there is the conference stored state as a conference room state, it is possible to review the conference after the conference is closed. For example, even a user who did not join the conference can know contents of the conference later.

In addition, in the network conference system 10 shown in FIG. 1, the medical image delivery server 100 includes the comment information holding unit 103. In the comment information holding unit 103, comment information given during the conference is held so as to be correlated with the conference, and thus is differentiated from comment information given at other times. For this reason, it is possible to easily differentiate whether or not comment information given to medical image data is added during the conference, and thus, for example, an inspection right to the comment information of a user can be divided.

Further, in the network conference system 10 shown in FIG. 1, the medical image delivery server 100 includes the medical image processing unit 104 which performs a process for smoothly inspecting medical images. Therefore, the client terminals can smoothly inspect medical images. In addition, the medical image processing unit 104 preferentially processes medical image data which is scheduled to be used in a conference. For this reason, particularly, the client terminal can access the medical image data which is scheduled to be used in a conference and smoothly inspect medical images.

In the network conference system 10 shown in FIG. 1, the medical image delivery server 100 includes the conference operation history data holding unit 106 holding operation history data during a conference. Therefore, after a conference is closed, the conference can be replayed (reproduced) using the held conference operation history data, and thus the closed conference can be reviewed.

In addition, in the network conference system 10 shown in FIG. 1, the medical image delivery server 100 includes the medical image mark information holding unit 105 holding mark information which is selectively given to medical image data held by the medical image holding unit 102. Therefore, for example, when a conference room is generated, it is possible to easily search for necessary medical image data by narrowing down image data using the mark information.

In the network conference system 10 shown in FIG. 1, the medical image delivery server 100 includes, for example, the time marker holding unit 107 which holds time markers indicating remarkable points on the time axis given to a conference. Therefore, when a conference is replayed, it is possible to know remarkable points of the conference on the time axis through the time markers.

In addition, in the network conference system 10 shown in FIG. 1, a conference room in the conference room management unit 101 is transitioned from a conference stored state to a conference scheduled state in response to a resuming state. For this reason, it is possible to resume a closed conference. Further, in response to the resuming operation, a conference room may be transitioned from a conference stored state to a conference live state.

In the network conference system 10 shown in FIG. 1, it is determined whether or not predetermined medical image data is correlated with a conference room when a client terminal instructs the medical image data held in the medical image holding unit 102 to be deleted. If the medical image data is correlated with the conference room, the medical image holding unit 102 of the medical image delivery server 100 transmits a warning message to the client terminal. For this reason, it is possible to prevent a case where a user deletes necessary medical image data by mistake.

2. Modified Example

In the above-described embodiment, an example where the conference room management unit 101 manages the conference scheduled state and the conference stored state in addition to the conference live state as a conference room state has been described. However, there may be only the conference scheduled state, or there may be only the conference stored state, in addition to the conference live state.

The present disclosure contains subject matter related to that disclosed in Japanese Priority Patent Application JP 2010-230632 filed in the Japan Patent Office on Oct. 13, 2010, the entire contents of which are hereby incorporated by reference.

It should be understood by those skilled in the art that various modifications, combinations, sub-combinations and alterations may occur depending on design requirements and other factors insofar as they are within the scope of the appended claims or the equivalents thereof.

What is claimed is:

1. A server system connected to a client terminal via a network, the server system comprising:
at least one storage device configured to store medical image data and operation history data, wherein the medical image data and the operation history data are linked to a conference, and
at least one processor configured to manage a conference room for holding the conference, and configured to manage a plurality of states of the conference comprising a conference live state, a conference scheduled state and a conference stored state, wherein the conference scheduled state occurs prior to the conference and the conference stored state occurs after the conference live state,
wherein the server system is configured to allow a person who is scheduled to join the conference to inspect a medical image linked to the conference in advance of a transition to the conference live state,
wherein the at least one storage device is configured to store first comment information and second comment information related to the medical image data, and
wherein access rights to access the first comment information received during the conference is different from the access rights to access the second comment information received prior to the conference.

2. The server system according to claim 1, further comprising an image processing unit configured to perform a process for smoothly displaying a medical image in the client terminal, for the medical image data held in the at least one storage device.

3. The server system according to claim 2, wherein the image processing unit is configured to preferentially perform the process for the medical image data, which is scheduled to be used in the conference.

4. The server system according to claim 3, wherein the at least one storage device comprises a hard disk drive (HDD) and a solid state drive (SSD) as a storage medium, and wherein the image processing unit is configured to copy or move the medical image data, which is scheduled to be used in the conference, from the HDD to the SSD.

5. The server system according to claim 1, wherein the at least one storage device is configured to store mark information, which is selectively given to a predetermined number of the medical image data held in the at least one storage device.

6. The server system according to claim 1, wherein the at least one storage device is configured to hold the operation history data during the conference.

7. The server system according to claim 1, wherein the at least one storage device is configured to hold time markers indicating remarkable points given to the conference on a time axis.

8. The server system according to claim 7, wherein the time markers comprise a first time marker given during the conference and/or a second time marker given during replay of the conference, and wherein the at least one storage device is configured to store and display the first time marker and the second time marker so as to be differentiated from each other.

9. The server system according to claim 1, wherein the at least one processor is configured to resume a closed conference by transitioning a conference room state.

10. The server system according to claim 9, wherein the at least one processor is configured to resume a closed conference by transitioning the conference room state from the conference stored state to the conference scheduled state or to the conference live state.

11. The server system according to claim 9, wherein the at least one storage device is configured to store the operation history data during the conference, the operation history data being obtained by adding first operation history data during a conference of the resumed conference to second operation history data during a conference of the closed conference.

12. The server system according to claim 1, wherein the at least one processor is configured to generate a confirmation message when medical image data instructed to be deleted is linked to the conference.

13. The server system according to claim 1, wherein the at least one storage device is configured to permit a user with access rights to access the medical image data linked to the conference.

14. The server system according to claim 1, wherein the at least one storage device is configured to receive the second comment information relating to the medical image data prior to the conference.

15. The server system according to claim 1, wherein the first comment information is differentiated from the second comment information.

16. The server system according to claim 1, wherein the at least one storage device is configured to store mark information given to the medical image data, wherein the medical image data is searched based on the mark information.

17. A conference room management method, the method comprising:
  in a server connected to a client terminal via a network:
    storing medical image data and operation history data, wherein the medical image data and the operation history data are linked to a conference;
    managing a plurality of states of a conference room for holding the conference,
    wherein the plurality of states comprises conference live state, a conference scheduled state and a conference stored state, wherein the conference scheduled state occurs prior to the conference and the conference stored state occurs after the conference live state;
    allowing a person who is scheduled to join the conference to inspect a medical image linked to the conference in advance of a transition to the conference live state; and
    storing first comment information and second comment information related to the medical image data,
    wherein access rights to access the first comment information received during the conference is different from the access rights to access the second comment information received prior to the conference.

18. A network conference system comprising:
  a server system; and
  a client terminal that is connected to the server system via at least one network, wherein the server system comprises:
  at least one storage device configured to store medical image data and operation history data, wherein the medical image data and the operation history data are linked to a conference, and
  at least one processor configured to manage a conference room for holding the conference, and manage a plurality of states of the conference comprising a conference live state, a conference scheduled state and a conference stored state, wherein the conference scheduled state occurs prior to the conference and the conference stored state occurs after the conference live state,
  wherein the server system is configured to allow a person who is scheduled to join the conference to inspect a medical image linked to the conference in advance of a transition to the conference live state,
  wherein the at least one storage device is configured to store first comment information and second comment information related to the medical image data, and
  wherein access rights to access the first comment information received during the conference is different from the access rights to access the second comment information received prior to the conference.

* * * * *